US008043828B2

(12) United States Patent
Bodie et al.

(10) Patent No.: US 8,043,828 B2
(45) Date of Patent: Oct. 25, 2011

(54) MODIFIED ENDOGLUCANASE II AND METHODS OF USE

(75) Inventors: Elizabeth A. Bodie, San Carlos, CA (US); Andre Krouwer, Poeldijk (NL)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/523,353

(22) PCT Filed: Jan. 11, 2008

(86) PCT No.: PCT/US2008/000379
§ 371 (c)(1),
(2), (4) Date: Apr. 1, 2010

(87) PCT Pub. No.: WO2008/088724
PCT Pub. Date: Jul. 24, 2008

(65) Prior Publication Data
US 2010/0196954 A1 Aug. 5, 2010

Related U.S. Application Data

(60) Provisional application No. 60/881,280, filed on Jan. 18, 2007, provisional application No. 60/881,626, filed on Jan. 19, 2007.

(51) Int. Cl.
*C12Q 1/34* (2006.01)
(52) U.S. Cl. .......................................... 435/18
(58) Field of Classification Search .................. 435/183, 435/18
See application file for complete search history.

(56) References Cited

U.S. PATENT DOCUMENTS

| | | | |
|---|---|---|---|
| 4,261,868 A | 4/1981 | Hora et al. |
| 4,404,128 A | 9/1983 | Anderson |
| 4,613,406 A | 9/1986 | Gess |
| 4,832,864 A | 5/1989 | Olson |
| 4,923,565 A | 5/1990 | Fuentes et al. |
| 5,147,642 A | 9/1992 | Lotz et al. |
| 5,204,015 A | 4/1993 | Caldwell et al. |
| 5,232,851 A | 8/1993 | Cox et al. |
| 5,246,853 A | 9/1993 | Clarkson et al. |
| 5,254,283 A | 10/1993 | Arnold et al. |
| 5,314,692 A | 5/1994 | Haarasilta et al. |
| 5,472,864 A | 12/1995 | Bower |
| 5,475,101 A | 12/1995 | Ward et al. |
| 5,612,055 A | 3/1997 | Bedford et al. |
| 5,654,193 A | 8/1997 | Clarkson et al. |
| 6,268,169 B1 | 7/2001 | Fahnestock |
| 6,426,410 B1 | 7/2002 | Wang |

FOREIGN PATENT DOCUMENTS

| | | |
|---|---|---|
| JP | 07-203960 A2 | 8/1995 |
| WO | WO 91/14819 A1 | 10/1991 |
| WO | WO 91/14822 A1 | 10/1991 |
| WO | WO 91/17235 A1 | 11/1991 |
| WO | WO 92/06209 A1 | 4/1992 |
| WO | WO 92/17573 A1 | 10/1992 |
| WO | WO 92/17574 A1 | 10/1992 |
| WO | WO 92/18688 A1 | 10/1992 |
| WO | WO 93/20278 A1 | 10/1993 |
| WO | WO 95/09225 A1 | 4/1995 |
| WO | WO 96/23928 A1 | 8/1996 |

OTHER PUBLICATIONS

Altschul, S.F., et al. "Basic local alignment search tool." *J. Mol. Biol* 215(3): 403-410, 1990.
Bhikhabhai, R, et al., "Isolation of cellulolytic enzymes from *Trichoderma reesei* QM 9414." *J. Appl. Biochem.* 6(5-6): 336-45, 1984.
Brumbauer, A. et al., "Fractionation of cellulose and β-glucosidase in a *Trichoderma reesei* culture liquid by use of two-phase partitioning." *Bioseparation* 7(6): 287-295, 1999.
Campbell, E.I. et al., "Improved transformation efficiency of *Aspergillus niger* using the homologous *nia*D gene for nitrate reductase." *Current Genetics* 16(1): 53-56, 1989.
Cummings, C. et al., "Secretion of *Trichoderma reesei* β-glucosidase by *Saccharomyces cerevisiae*." *Current Genetics* 29(3): 227-233, 1996.
Database EMBL. "*Trichoderma viride* strain AS 3.3711 endoglucanase III (EGIII) mRNA,complete cds." Accession No. AY343987, 2003.
Database UniProt. "SubName: Full=Endoglucanase III." Accession No. Q7Z7X2, 2003.
Deutscher, M.P., "Rethinking your purification procedure." In *Guide to Protein Purification*, Methods in Enzymology, No. 182, ed. M.P. Deutscher. New York: Academic Press, pp. 779-780, 1990.
Ellouz, S. et al., "Analytical separation of *Trichoderma reesei* celluloses by ion-exchange fast protein liquid chromatography." *J. Chromatography* 396: 307-317, 1987.
Fliess, A. et al., "Characterization of celluloses by HPLC separation," *Appl. Microbiol. Biotechnol.* 17(5): 314-318, 1983.
Ghose, T.K., "Measurement of cellulose activities." *Pure and Applied Chemistry* 59(2): 257-268, 1987.
Goyal, A. et al., "Characterisation of fungal celluloses." *Biores. Technol* 36: 37-50, 1991.
Van Den Hondel. C. et al., "Heterologous gene expression in filamentous fungi." In *More Gene Manipulations in Fungi*, eds. J.W. Bennett et al. San Diego, CA: Academic Press, pp. 396-428, 1991.
Hu, Q.J. et al., "Antibodies specific for the human retinoblastoma protein identify a family of related polypeptides.." Mol. Cell. Biol. 11(11): 5792-5799, 1991.
Ilmen, M. et al., "Regulation of cellulase gene expression in the filamentous fungus *Trichoderma reesei*." *Appl. Environ. Microbiol.* 63(4): 1298-1306, 1997.
Li, X.-L. et al., "Expression of Aureobasidium pullulans xynA in, and secretion of the xylanase from, *Saccharomyces cerevisiae*." *Appl. Environ. Microbiol.* 62(1): 200-213, 1996.
Medve, J. et al., "Ion-exchange chromatographic purification and quantitative analysis of *Trichoderma reesei* cellulases cellobiohydrolase I, II and endoglucanase II by fast protein liquid chromatography." *J. Chromat. A* 808(1-2): 153-165, 1998.
Ortega, N, et al., "Kinetics of cellulose saccharification by *Trichoderma reesei* cellulases." *International Biodeterioration & Biodegradation* 47(1): 7-14, 2001.

(Continued)

*Primary Examiner* — Maryam Monshipouri

(57) ABSTRACT

Described herein is a modified EGII cellulase having the amino acid sequence shown in SEQ ID NO:1, compositions comprising the modified EGII and methods of use.

13 Claims, 6 Drawing Sheets

OTHER PUBLICATIONS

Penttilä, M. et al., "Homology between cellulase genes of *Trichoderma reesei*: complete nucleotide sequence of the endoglucanase I gene." *Gene* 45(3): 253-63, 1986.

Penttilä, M.E. et al., "Efficient secretion of two fungal cellobiohydrolases by *Saccharomyces cerevisiae*." *Gene* 63(1): 103-112, 1988.

Pourquié, J. et al., "Scale up of cellulase production and utilization." In *Biochemistry and Genetics of Cellulose Degradation*, eds. J.P. Aubert et al. London: Academic Press, pp. 71-86, 1988.

Van Rensburg, P. et al., "Engineering yeast for efficient cellulose degradation." *Yeast* 14(1): 67-76, 1998.

Rothstein, S.J. et al., "Synthesis and secretion of wheat alpha-amylase in *Saccharomyces cerevisiae*." *Gene* 55(2-3): 353-356, 1987.

Saloheimo, M. et al., "EGIII, a new endoglucanase from *Trichoderma reesei*: the characterization of both gene and enzyme," *Gene* 63(1): 11-22, 1988.

Schulein, M., "Cellulases of *Trichoderma reesei*." *Methods in enzymology* 160: 234-242, 1988.

Scopes, R.K. et al., "Purification of all glycolytic enzymes from one muscle extract." In *Carbohydrate Metabolism—Part E*, Methods in Enzymology, No. 90, ed. W.A. Wood. New York: Academic Press, pp. 479-490, 1982.

Sheir-Neiss, G. et al., "Characterization of the secreted cellulases of *Trichoderma reesei* wild type and mutants during controlled fermentations." *Applied Microbiology and Biotechnology* 20(1): 46-53, 1984.

Shoemaker, S.P. et al., "Enzymic activities of endo-1,4-beta-D-glucanases purified from *Trichoderma viride*." *Biochimica et Biophysica Acta (BBA)—Enzymology* 523(1): 133-146, 1978.

Smith, J.L. et al., "Sequence of the cloned *pyr4* gene of *Trichoderma reesei* and its use as a homologous selectable marker for transformation." *Current Genetics* 19(1): 27-33, 1991.

Stalbrand, H. et al., "Cloning and expression in *Saccharomyces cerevisiae* of a *Trichoderma reesei* beta-mannanase gene containing a cellulose binding domain." *Appl. Environ. Microbiol.* 61(3): 1090-1097, 1995.

Suurnäkki, A. et al., "*Trichoderma reesei* cellulases and their core domains in the hydrolysis and modification of chemical pulp." *Cellulose* 7(2): 189-209, 2000.

Te'o, V.S.J. et al., "Codon optimization of xylanase gene xyn B from the thermophilic bacterium *Dictyoglomus thermophilum* for expression in the filamentous fungus *Trichoderma reesei*." *FEMS Microbiology Letters* 190(1): 13-19, 2000.

Van Tilbeurgh, H. et al., "Separation of endo- and exo-type cellulases using a new affinity chromatography method." *FEBS Letters* 169(2): 215-218, 1984.

Tomaz, C.T. et al. "Studies on the chromatographic fractionation of *Trichoderma reesei* cellulases by hydrophobic interaction." *J. Chromat. A* 865(1-2): 123-128, 1999.

Wood, Thomas M. et al., "Methods for measuring cellulase activities." In *Biomass Part A: Cellulose and Hemicellulose*, Methods in Enzymology, No. 160, eds. W.A. Wood et al. New York: Academic Press, pp. 87-112, 1988.

International Search Report and Written Opinion of the International Searching Authority of International Application No. PCT/US2008/000379 dated Oct. 28, 2008.

Protein Sequence for EG2 (SEQ ID NO:1)

| | | | | | |
|---|---|---|---|---|---|
| MNKSVAPLLL | AASILYGGAA | AQQTVWGQCG | GIGWSGPTNC | APGSACSTLN | 50 |
| PYYAQCIPGA | TTITTSTRPP | SGPTTTTRAT | STSSSTPPTS | SGVRFAGVNI | 100 |
| AGFDFGCTTD | GTCVTSKVYP | PLKNFTGSNN | YPDGIGQMQH | FVNDDGMTIF | 150 |
| RLPVGWQYLV | NNNLGGNLDS | TSISKYDQLV | QGCLSLGAYC | IVDIHNYARW | 200 |
| NGGIIGQGGP | TNAQFTSLWS | QLASKYASQS | RVWFGIMNEP | HDVNINTWAA | 250 |
| TVQEVVTAIR | NAGATSQFIS | LPGNDWQSAG | AFISDGSAAA | LSQVTNPDGS | 300 |
| TTNLIFDVHK | YLDSDNSGTH | AECTTNNIDG | AFSPLATWLR | QNNRQAILTE | 350 |
| TGGGNVQSCI | QDMCQQIQYL | NQNSDVYLGY | VGWGAGSFDS | TYVLTETPTG | 400 |
| SGNSWTDTSL | VSSCLARK | | | | 468 |

*FIG. 1*

DNA Sequence for EG2 (SEQ ID NO:2)

| | | | | | |
|---|---|---|---|---|---|
| ATGAACAAGT | CCGTGGCTCC | ATTGCTGCTT | GCAGCGTCCA | TACTATATGG | 50 |
| CGGCGCCGCT | GCACAGCAGA | CTGTCTGGGG | CCAGTGTGGA | GGTATTGGTT | 100 |
| GGAGCGGACC | TACGAATTGT | GCTCCTGGCT | CAGCTTGTTC | GACCCTCAAT | 150 |
| CCTTATTATG | CGCAATGTAT | TCCGGGAGCC | ACTACTATCA | CCACTTCGAC | 200 |
| CCGGCCACCA | TCCGGTCCAA | CCACCACCAC | CAGGGCTACC | TCAACAAGCT | 250 |
| CATCAACTCC | ACCCACGAGC | TCTGGGGTCC | GATTTGCCGG | CGTTAACATC | 300 |
| GCGGGTTTTG | ACTTTGGCTG | TACCACAGAG | TGAGTACCCT | TGTTTCCTGG | 350 |
| TGTTGCTGGC | TGAAAAGTTG | GGCGGGTATA | CAGCGATGCG | GACTGCAAGA | 400 |
| ACACCGCCGG | TCCGCCACCA | TCAAGATGTG | GGTGGTAAGC | GGCGGTGTTT | 450 |
| TGTACAACTA | CCTGACAGCT | CACTCAGGAA | CTGAGAATTA | ATGGAAGTCT | 500 |
| TGTTACAGTG | GCACTTGCGT | TACCTCGAAG | GTTTATCCTC | CGTTGAAGAA | 550 |
| CTTCACCGGC | TCAAACAACT | ACCCCGATGG | CATCGGCCAG | ATGCAGCACT | 600 |
| TCGTCAACGA | CGACGGGATG | ACTATTTTCC | GCTTACCTGT | CGGATGGCAG | 650 |
| TACCTCGTCA | ACAACAATTT | GGGCGGCAAT | CTTGATTCCA | CGAGCATTTC | 700 |
| CAAGTATGAT | CAGCTTGTTC | AGGGGTGCCT | GTCTCTGGGC | GCATACTGCA | 750 |
| TCGTCGACAT | CCACAATTAT | GCTCGATGGA | ACGGTGGGAT | CATTGGTCAG | 800 |
| GGCGGCCCTA | CTAATGCTCA | ATTCACGAGC | CTTTGGTCGC | AGTTGGCATC | 850 |
| AAAGTACGCA | TCTCAGTCGA | GGGTGTGGTT | CGGCATCATG | AATGAGCCCC | 900 |
| ACGACGTGAA | CATCAACACC | TGGGCTGCCA | CGGTCCAAGA | GGTTGTAACC | 950 |
| GCAATCCGCA | ACGCTGGTGC | TACGTCGCAA | TTCATCTCTT | TGCCTGGAAA | 1000 |
| TGATTGGCAA | TCTGCTGGGG | CTTTCATATC | CGATGGCAGT | GCAGCCGCCC | 1050 |
| TGTCTCAAGT | CACGAACCCG | GATGGGTCAA | CAACGAATCT | GATTTTTGAC | 1100 |
| GTGCACAAAT | ACTTGGACTC | AGACAACTCC | GGTACTCACG | CCGAATGTAC | 1150 |
| TACAAATAAC | ATTGACGGCG | CCTTTTCTCC | GCTTGCCACT | TGGCTCCGAC | 1200 |
| AGAACAATCG | CCAGGCTATC | CTGACAGAAA | CCGGTGGTGG | CAACGTTCAG | 1250 |
| TCCTGCATAC | AAGACATGTG | CCAGCAAATC | CAATATCTCA | ACCAGAACTC | 1300 |
| AGATGTCTAT | CTTGGCTATG | TTGGTTGGGG | TGCCGGATCA | TTTGATAGCA | 1350 |
| CGTATGTCCT | GACGGAAACA | CCGACTGGCA | GTGGTAACTC | ATGGACGGAC | 1400 |
| ACATCCTTGG | TCAGCTCGTG | TCTCGCAAGA | AAGTAG | | 1436 |

*FIG. 2*

ClustalV Alignment

```
              MNKSVAPLLLAASILYGGAAAQQTVWGQCGGIGWSGPTNCAPGSACSTLNPYYAQCIPGATTITTSTRPP
                       10        20        30        40        50        60        70
EG2-1988      MNKSVAPLLLAASILYGGAVAQQTVWGQCGGIGWSGPTNCAPGSACSTLNPYYAQCIPGATTITTSTRPP  70
mEG2          MNKSVAPLLLAASILYGGAAAQQTVWGQCGGIGWSGPTNCAPGSACSTLNPYYAQCIPGATTITTSTRPP  70

SGPTTTTRATSTSSSTPPTSSGVRFAGVNIAGFDFGCTTDGTCVTSKVYPPLKNFTGSNNYPDGIGQMQH
                       80        90       100       110       120       130       140
EG2-1988      SGPTTTTRATSTSSSTPPTSSGVRFAGVNIAGFDFGCTTDGTCVTSKVYPPLKNFTGSNNYPDGIGQMQH 140
mEG2          SGPTTTTRATSTSSSTPPTSSGVRFAGVNIAGFDFGCTTDGTCVTSKVYPPLKNFTGSNNYPDGIGQMQH 140

FVNDDGMTIFRLPVGWQYLVNNNLGGNLDSTSISKYDQLVQGCLSLGAYCIVDIHNYARWNGGIIGQGGP
                      150       160       170       180       190       200       210
EG2-1988      FVNEDGMTIFRLPVGWQYLVNNNLGGNLDSTSISKYDQLVQGCLSLGAYCIVDIHNYARWNGGIIGQGGP 210
mEG2          FVNDDGMTIFRLPVGWQYLVNNNLGGNLDSTSISKYDQLVQGCLSLGAYCIVDIHNYARWNGGIIGQGGP 210

TNAQFTSLWSQLASKYASQSRVWFGIMNEPHDVNINTWAATVQEVVTAIRNAGATSQFISLPGNDWQSAG
                      220       230       240       250       260       270       280
EG2-1988      TNAQFTSLWSQLASKYASQSRVWFGIMNEPHDVNINTWAATVQEVVTAIRNAGATSQFISLPGNDWQSAG 280
mEG2          TNAQFTSLWSQLASKYASQSRVWFGIMNEPHDVNINTWAATVQEVVTAIRNAGATSQFISLPGNDWQSAG 280

AFISDGSAAALSQVTNPDGSTTNLIFDVHKYLDSDNSGTHAECTTNNIDGAFSPLATWLRQNNRQAILTE
                      290       300       310       320       330       340       350
EG2-1988      AFISDGSAAALSQVTNPDGSTTNLIFDVHKYLDSDNSGTHAECTTNNIDGAFSPLATWLRQNNRQAILTE 350
mEG2          AFISDGSAAALSQVTNPDGSTTNLIFDVHKYLDSDNSGTHAECTTNNIDGAFSPLATWLRQNNRQAILTE 350

TGGGNVQSCIQDMCQQIQYLNQNSDVYLGYVGWGAGSFDSTYVLTETPTSSGNSWTDTSLVSSCLARK
                      360       370       380       390       400       410
EG2-1988      TGGGNVQSCIQDMCQQIQYLNQNSDVYLGYVGWGAGSFDSTYVLTETPTSSGNSWTDTSLVSSCLARK 418
mEG2          TGGGNVQSCIQDMCQQIQYLNQNSDVYLGYVGWGAGSFDSTYVLTETPTGSGNSWTDTSLVSSCLARK 418
```

FIG. 3

SDS-PAGE

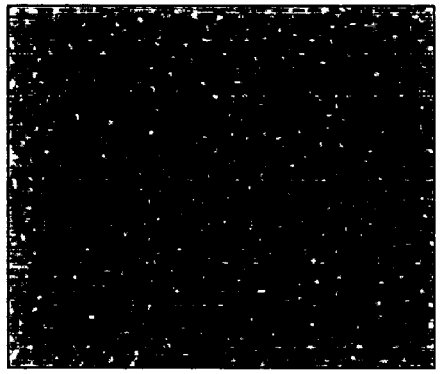
113,176 CMC U IndiAge MAX
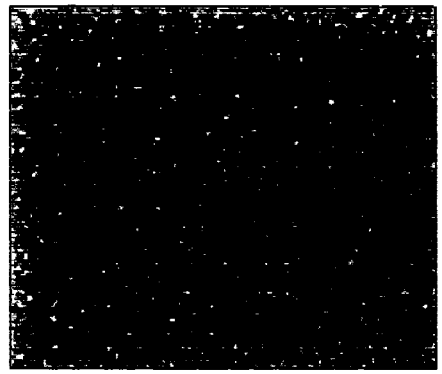
113,176 CMC U Modified EG2
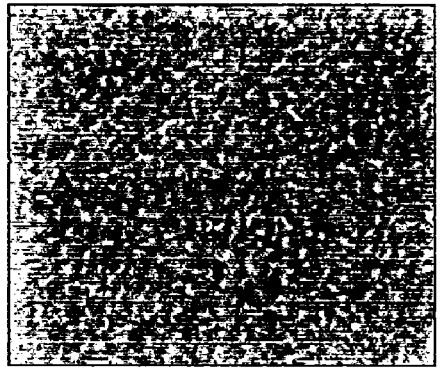
213,579 CMC U IndiAge MAX
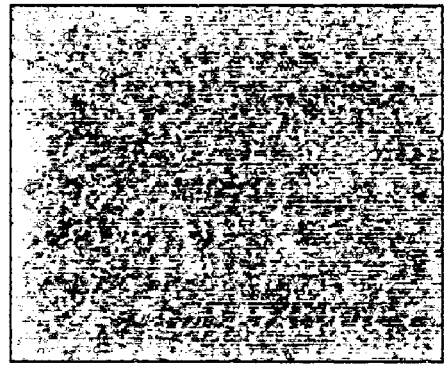
213,579 CMC U Modified EG2
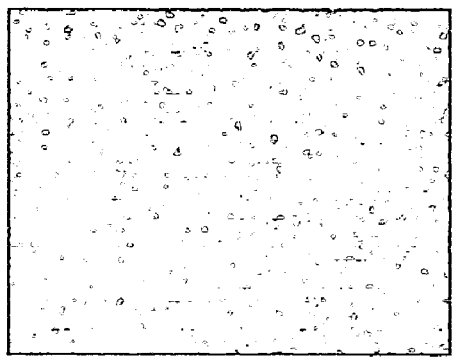
313,830 CMC U IndiAge MAX
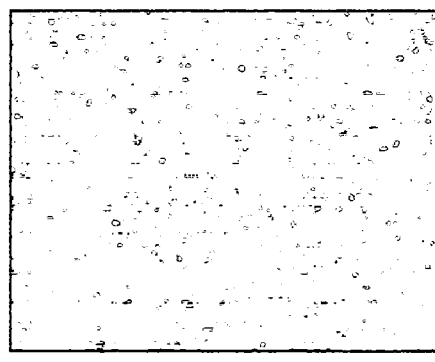
313,830 CMC U Modified EG2
FIG. 8

MODIFIED ENDOGLUCANASE II AND METHODS OF USE

CROSS-REFERENCES TO RELATED APPLICATIONS

The present application is a 371 of PCT/US2008/000379, filed Jan. 1, 2008, which claims benefit of and priority to U.S. Provisional Application Ser. No. 60/881,280, filed Jan. 18, 2007, and U.S. Provisional Application Ser. No. 60/881,626, filed Jan. 19, 2007, both of which are incorporated herein by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

Described herein is a modified endoglucanase II (EGII) derived from *Trichoderma reesei*, compositions comprising said EGII and methods for treating textiles using said composition. Provided for herein are novel enzyme preparations comprising an enzyme exhibiting endoglucanase activity which performs very well in industrial applications such as laundry compositions, for biopolishing of newly manufactured textiles; for providing an abraded look of cellulosic fabric or garment, and for treatment of paper pulp. Further, the invention relates to DNA constructs encoding such enzymes, a method for providing a gene encoding for such enzymes, a method of producing the enzymes: enzyme preparations containing such enzymes, and the use of these enzymes for a number of industrial applications. Thus, the present application also provides improved methods for treating cotton-containing fabrics and non-cotton containing cellulose fabrics with cellulase as well as to the fabrics produced from these methods. In particular, the improved methods of the present invention are directed to contacting cotton-containing fabrics and non-cotton containing fabrics with an aqueous solution containing a cellulase composition which comprises a modified EGII cellulase enzymes.

BACKGROUND OF THE INVENTION

Cellulases or cellulytic enzymes are enzymes involved in hydrolyses of cellulose. In the hydrolysis of native cellulose, it is known that there are three major types of cellulase enzymes involved, namely cellobiohydrolase (1,4-β-D-glucan cellobiohydrolase, EC 3.2.1.91), endo-β-1,4-glucanase (endo-1,4-β-D-glucan β-glucanohydrolase, EC 3.2.1.4) and β-glucosidase (EC 3.2.1.21).

Cellulases are synthesized by a large number of microorganisms which include fungi, actinomycetes, myxobacteria and true bacteria but also by plants. Especially endoglucanases of a wide variety of specificities have been identified.

A very important industrial use of cellulytic enzymes is the use for treatment of cellulosic textile or fabric, e.g. as ingredients in detergent compositions or fabric softener compositions, for bio-polishing of new fabric (garment finishing), and for obtaining a "stone-washed" look of cellulose-containing fabric, especially denim, and several methods for such treatment have been suggested.

An object of the present invention is to provide novel enzyme preparations having substantial cellulytic activity at acid or neutral conditions and improved performance in paper pulp processing, textile treatment, laundry processes or in animal feed; preferably novel cellulases, more preferably well-performing endoglucanases, which are contemplated to be producible or produced by recombinant techniques.

Most newly manufactured cotton fabrics and cotton blend fabrics have a handle that is rather hard and stiff unless they are treated with finishing components. Furthermore, the fabric surface is not always smooth due to small fuzzy fibers protruding from the individual cotton fibers. In addition, after a relatively short period of wear, collections of lint appear on the surface (surface linting) giving the appearance of "pills" on the surface which causes the fabric to have an unappealing, worn look. In polyester fabrics, this phenomena is actually "pilling" and provides a similar unappealing fabric appearance. The term "pilling" will also apply to cellulosic fabrics in the instant application.

Thus, a useful feature of cellulases in the treatment of textiles is their ability to recondition used fabrics by making their colors more vibrant. For example, repeated washing of cotton containing fabrics results in a greyish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Cellulase treatment of the fabric surface improves fabric quality with respect to handle and appearance without loss of fabric wettability. The most important effects are less fuzz and pilling, increased gloss/luster, improved fabric handle, increased durable softness and improved water absorbency. These effects are referred to as biopolishing effects.

Despite knowledge in the art related to many cellulase compositions, there is a continued need for new cellulases having a varying spectrum of characteristics which are useful in, for example, treating textiles, as a component of detergent compositions, in the treatment of pulp and paper, and in the conversion of biomass.

The cellulase compositions described herein provide improved performance characteristics, especially in textile processing.

BRIEF SUMMARY OF THE INVENTION

It has been found, surprisingly, that treating cellulosic goods with a *Trichoderma* cellulase enzyme composition consisting essentially of a modified EGII component offers superior performance compared to endo-enriched cellulase compositions. By using specific enzyme compositions described herein, the removal of pills is more efficient, abrasion is enhanced and the amount of fabric destruction during enzyme treatment is reduced, relative to standard commercial cellulase enzymes used presently for treating cotton fabrics during manufacture. The invention thereby consists of a method for treating cotton fabrics using specified cellulase compositions.

In an embodiment the cellulase enzyme composition consists essentially of a modified EGII component. In one aspect the enzyme composition comprises at least 80% modified EGII component. In a second aspect, the enzyme composition comprises at least 90% modified EGII component. In a third aspect, the enzyme composition comprises at least 95% modified EGII component. In a further aspect, the enzyme composition comprises at least 97% modified EGII component.

In another embodiment, the modified EGII component is substantially pure.

In an embodiment, the modified EGII component is formulated as a cellulase enzyme composition. In one aspect the modified EGII component is a part of a treating composition. In a second aspect the modified EGII component is a part of a detergent composition.

In an embodiment a method of treating cellulosic fabrics using specified cellulase compositions is provided. The method comprises the steps of (a) contacting said cellulose containing fabric with a treating composition comprising an effective amount of a cellulase; and (b) incubating said cellulose containing fabric in contact with said cellulase under conditions effective to treat said fabric. In one aspect the cellulase comprises a modified EGII component.

In another embodiment there is provided an isolated DNA encoding the amino acid sequence provided in FIG. 1. In one aspect the DNA has the sequence provided in SEQ ID NO:2.

In one embodiment the invention includes an isolated polynucleotide having a sequence which encodes modified EG2, a sequence complementary to the egl2 gene coding sequence, and/or a composition comprising the polynucleotide. The polynucleotide may be mRNA, DNA, cDNA, genomic DNA, or an antisense analog thereof.

In another embodiment, a egl2 polynucleotide may comprise an isolated nucleic acid molecule which hybridizes to the complement of the nucleic acid presented as SEQ ID NO:2 under moderate to high stringency conditions, where the nucleic acid molecule encodes a modified EG2 polypeptide that exhibits endoglucanase activity.

In another embodiment, the polynucleotide has at least 80%, 85%, 90%, 95%, 98% or more sequence identity to the sequence presented as SEQ ID NO:2 and encodes a modified EG2 protein. In a specific embodiment, the polynucleotide comprises a sequence substantially identical to SEQ ID NO:2. The invention also contemplates fragments of the polynucleotide, preferably at least about 15-30 nucleotides in length.

In a second aspect, modified EG2 polypeptides or proteins comprise a sequence having at least 80%, 85%, 90%, 95%, 98% or more sequence identity to the sequence presented as SEQ ID NO:1.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

The invention further provides recombinant expression vectors containing a nucleic acid sequence encoding modified EG2 or a fragment or splice variant thereof, operably linked to regulatory elements effective for expression of the protein in a selected host. In a related aspect, the invention includes a host cell containing the vector.

In a fifth aspect the present invention relates to a recombinant host cell comprising the nucleic acid construct of the invention.

The invention further includes a method for producing modified EG2 by recombinant techniques, by culturing recombinant prokaryotic or eukaryotic host cells comprising nucleic acid sequence encoding modified EG2 under conditions effective to promote expression of the protein, and subsequent recovery of the protein from the host cell or the cell culture medium.

In a sixth aspect the present invention relates to a method for producing a polypeptide of the invention, the method comprising: (a) cultivating a microorganism capable of producing the polypeptide; and (b) recovering the polypeptide.

Further provided herein are analytical methods for detecting egl12 nucleic acids and modified EG2 proteins also form part of the invention.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 illustrates the amino acid sequence of the modified EGII (SEQ ID NO:1) described herein.

FIG. 2 illustrates a nucleotide sequence encoding the amino acid sequence depicted in FIG. 1.

FIG. 3 is an alignment of the published EG2 (Gene (1988) 63(1):11-22) (labeled 'Eg2-1988') with the amino acid sequence described herein (labeled 'mEG2').

FIG. 8 are photographs showing the results of enzymatic treatment on depilling.

DETAILED DESCRIPTION

Figure 4:
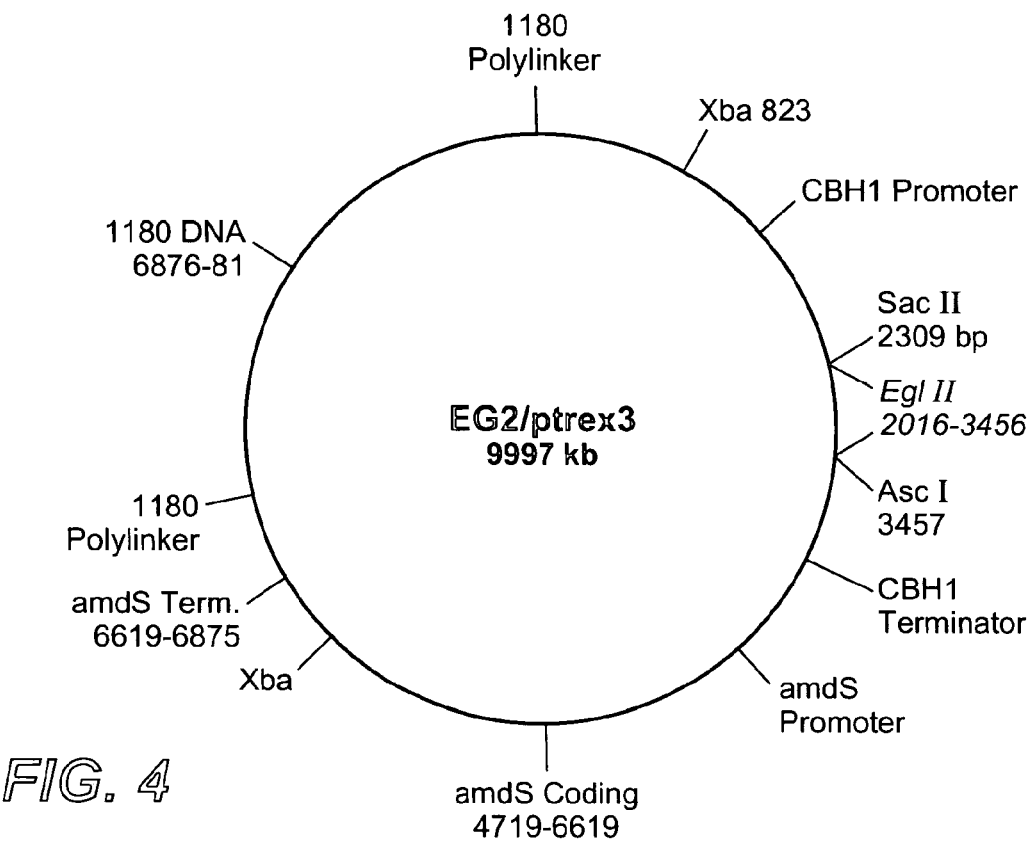
FIGS. 4 and 5 are schematics of the EGIIpTrex3 plasmid used to express a modified EGII.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

DEFINITIONS

"Cotton-containing fabric" means sewn or unsewn fabrics made of pure cotton or cotton blends including cotton woven fabrics, cotton knits, cotton denims, cotton yarns and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Cellulose containing fabric" means any cotton or non-cotton containing cellulosic fabric or cotton or non-cotton containing cellulose blend including natural cellulosics and manmade cellulosics (such as jute, flax, ramie, rayon, TENCELT™). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Of course, included within the definition of cellulose containing fabric is any garment or yarn made of such materials. Similarly, "cellulose containing fabric" includes textile fibers made of such materials.

"Treating composition" means a composition comprising a modified EGII cellulase component which may be used in treating a cellulose containing fabric during manufacture. Such treating includes, but is not limited to, stonewashing, depilling, modifying the texture, feel and/or appearance of cellulose containing fabrics or other techniques used during manufacturing of cellulose containing fabrics. Additionally, treating within the context of this invention contemplates the removal of "dead cotton", from cellulosic fabric or fibers, i.e. immature cotton which is significantly more amorphous than mature cotton. Dead cotton is known to cause uneven dyeing. Additionally, "treating composition" means a composition comprising a modified EGII cellulase component which may be used in washing of a soiled manufactured cellulose containing fabric. For example, modified EGII cellulase may be used in a detergent composition for washing laundry. Detergent compositions useful in accordance with the present invention include special formulations such as pre-wash, pre-soak and home-use color restoration compositions. Treating compositions may be in the form of a concentrate which requires dilution or in the form of a dilute solution or form which can be applied directly to the cellulose containing fabric.

It is Applicants' present belief that the action pattern of cellulase upon cellulose containing fabrics does not differ significantly whether used as a stonewashing composition during manufacturing or during laundering of a soiled manufactured cellulose containing fabric. Thus, improved properties such as abrasion, redeposition of dye, strength loss and improved feel conferred by a certain cellulase or mixture of cellulases are obtained in both detergent and manufacturing processes incorporating cellulase. Of course, the formulations of specific compositions for the various textile applications of cellulase, e.g., stonewashing or laundry detergent or pre-soak, may differ due to the different applications to which the respective compositions are directed, as indicated herein. However, the improvements effected by the addition of cellulase compositions will be generally consistent through each of the various textile applications.

"Stonewashing composition" means a formulation for use in stonewashing cellulose containing fabrics. Stonewashing compositions are used to modify cellulose containing fabrics prior to presentation for consumer sale, i.e., during the manufacturing process, in contrast to detergent compositions which are intended for the cleaning of soiled garments.

"Stonewashing" means the treatment of colored cellulose containing fabric with a cellulase solution under agitating and cascading conditions, i.e., in a rotary drum washing machine, which impart a "stonewashed" appearance to the denim. Methods for imparting a stonewashed appearance to denim are described in U.S. Pat. No. 4,832,864 which is incorporated herein by reference in its entirety. Generally, stonewashing techniques have been applied to dyed denim.

"Detergent composition" means a mixture which is intended for use in a wash medium for the laundering of soiled cellulose containing fabrics. In the context of the present invention, such compositions may include, in addition to cellulases and surfactants, many additives, including, but not limited to, additional hydrolytic enzymes, builders, bleaching agents, bluing agents and fluorescent dyes, caking inhibitors, masking agents, cellulase activators, antioxidants, and solubilizers may be included. Such compositions are generally used for cleaning soiled garments and are not used during the manufacturing process, in contrast to stonewashing compositions. "Redepositing cellulase" means cellulases which in the enzymatic stonewashing or other treatment of cellulose containing fabrics using cellulase solutions, particularly denim, result in redeposition of dye onto the substrate. This effect is often referred to as backstaining. Such backstaining of the fabric leads to incomplete stonewashing because instead of the desired blue on white contrast, the redeposition results in blue on blue.

"Surface active agent or surfactant" means anionic, nonionic and ampholytic surfactants well known for their use in detergent compositions.

"Wash medium" means an aqueous wash solution prepared by adding a requisite amount of a detergent composition to water. The wash medium generally contains a cleaning effective amount of the detergent.

The term "EGII" as defined herein refers to an endoglucanase type component typically derived from, or embodying the identifying characteristics of those derived from, EGII of *Trichoderma* sp. It is noted that EGII has been previously referred to by the nomenclature "EGIII" by some authors but current nomenclature uses the term EGII. See, for example, the discussion in Stalbrand, et al, APPLIED AND ENVIRONMENTAL MICROBIOLOGY, vol. 61, p. 1090-1097 (1995)). In any event, the EGII protein defined herein is substantially different from the EGIII protein in its molecular weight, pI and pH optimum. The term "EGII cellulase" refers to the endoglucanase component derived from *Trichoderma* spp. characterized by a pH optimum of about 4.0 to 6.0 an isoelectric point (pI) of from about 5.5, and a molecular weight of about 48 Kdaltons. Preferably, EGII cellulase is derived from either *Trichoderma reesei* or from *Trichoderma viride*.

The term "modified EGII" as used herein means the amino acid sequence shown in FIG. 1.

The term "% homology" is used interchangeably herein with the term "% identity" herein and refers to the level of nucleic acid or amino acid sequence identity between the nucleic acid sequence that encodes modified EGII or the modified EGII amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for modified egl II, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

A "component cellulase" is a component essentially free of other cellulase components usually occurring in a cellulase system produced by a given microorganism. The single component may be a recombinant component, i.e., produced by cloning of a DNA sequence encoding the single component and subsequent cell transformed with the DNA sequence and expressed in a host, see for example, U.S. Pat. No. 5,654,193. Other examples of component cellulases include but are not limited to those disclosed in JP-07203960-A and WO 92/06209. The host is preferably a heterologous host, but the host may under certain conditions also be the homologous host.

The term "purified" as used herein also refers to removal of other components, particularly other proteins and most particularly other enzymes present in the cell expressing the modified EGII. The modified EGII may be "substantially pure," that is, free from other components from the organism in which it is produced, that is, for example, a host organism for recombinantly produced modified EGII. In preferred embodiment, the modified EGII are at least 75% (w/w) pure, more preferably at least 80%, at least 85%, at least 90%, at least 95%, at least 96%, at least 97%, at least 98%, or at least 99% pure. In another preferred embodiment, the modified EGII is 100% pure.

The phrase "depilling treatment" refers to treatments carried out during the manufacturing process or in subsequent laundering. In either case, treatment is carried out by adding cotton goods to a rotating horizontal or vertical drum jet dyer, washing machine, or other device that contains the fabric, water, buffer, cellulase enzyme and, optionally, detergents or surfactants, while providing agitation and shear to the fabric. The treatment is often followed by a rinsing with water to remove the spent chemicals and debris from the fabric, including the loose fibrils. After treatment, the fabric is removed from the machine and dried.

The term "polypeptide" as used herein refers to a compound made up of a single chain of amino acid residues linked by peptide bonds. The term "protein" as used herein is used interchangably with the term "polypeptide".

The term "nucleic acid molecule" includes RNA, DNA and cDNA molecules. It will be understood that, as a result of the degeneracy of the genetic code, a multitude of nucleotide sequences encoding a given protein such as, for example, a modified EG2 (or any other protein) may be produced. The present invention contemplates every possible variant nucleotide sequence, encoding modified EG2, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode a novel protein as described herein or an analog or homologue thereof will hybridize, under moderate to high stringency conditions to the protein's corresponding nucleic acid sequence provided herein. However, in some cases a novel protein-encoding nucleotide sequence is employed that possesses a substantially different codon usage, while the protein encoded by the novel protein-encoding nucleotide sequence has the same or substantially the same amino acid sequence as the native protein. For example, the coding sequence may be modified to facilitate faster expression of the novel protein in a particular prokaryotic or eukaryotic expression system, in accordance with the frequency with which a particular codon is utilized by the host. Te'o, et al. FEMS Microbiology Letters 190:13-19, (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook et al., MOLECULAR CLONING: A LABORATORY MANUAL (Second Edition), Cold Spring Harbor Press, Plainview, N.Y., 1989, Chapters 9 and 11, and in Ausubel FM et al., CURRENT PROTOCOLS IN MOLECULAR BIOLOGY, John Wiley & Sons, New York, N.Y., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*.

As used herein, the term "purifying" generally refers to subjecting nucleic acid or protein containing cells to biochemical purification and/or column chromatography.

The terms "isolated" or "purified" as used herein refer to a nucleic acid or protein that is removed from at least one component with which it is naturally associated.

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

As used herein, the terms "active" and "biologically active" refer to a biological activity associated with a particular protein, such as the enzymatic activity associated with a protease. It follows that the biological activity of a given protein refers to any biological activity typically attributed to that protein by those of skill in the art.

As used herein, the term "enriched" means that the novel protein is found in a concentration that is greater relative to the novel protein concentration found in a wild-type, or naturally occurring, fungal cellulase composition.

Host Organisms and Culture Conditions

The use cells to express modified EGII, with no particular method of expression required, is contemplated herein.

The invention provides host cells which have been transduced, transformed or transfected with an expression vector comprising a modified EGII-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding a modified EGII, such that modified EGII is expressed in the cell line.

(i) Filamentous Fungi

The present invention provides filamentous fungi comprising cells which have been modified, selected and cultured in a manner effective to result in enhanced modified EGII production or expression relative to the corresponding non-transformed parental fungi.

Examples of species of parental filamentous fungi that may be treated and/or modified for enhanced modified EGII expression include, but are not limited to *Trichoderma*, e.g., *Trichoderma reesei, Trichoderma longibrachiatum, Trichoderma viride, Trichoderma koningii; Penicillium* sp., *Humicola* sp., including *Humicola insolens; Aspergillus* sp., *Chrysosporium* sp., *Fusarium* sp., *Hypocrea* sp., and *Emericella* sp.

Modified EGII expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71 86, 1988 and Ilmen, M. et al., Appl. Environ. Microbiol. 63:1298 1306, 1997. Culture conditions are also standard, e.g., cultures are incubated at 28° C. in shaker cultures or fermenters until desired levels of modified EGII expression are achieved.

Preferred culture conditions for a given filamentous fungus may be found in the scientific literature and/or from the source of the fungi such as the American Type Culture Collection (ATCC; go to world wide web atcc.org). After fungal growth has been established, the cells are exposed to conditions effective to cause or permit the over expression of modified EGII.

In cases where a modified EGII coding sequence is under the control of an inducible promoter, the inducing agent, e.g., a sugar, metal salt or antibiotics, is added to the medium at a concentration effective to induce high-level modified EGII expression.

(ii) Yeast

The present invention also contemplates the use of yeast as a host cell for modified EGII production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei* (Cummings and Fowler, 1996), a xylanase from Aureobasidlium pullulans (Li and Ljungdahl, 1996), an alpha-amylase from wheat (Rothstein et al., 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (BgI1) was successfully expressed in a laboratory strain of *S. cerevisiae* (Van Rensburg et al., 1998).

Nucleic Acid Constructs/Expression Vectors

Polynucleotide fragments encoding a modified EGII ("modified EGII-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of a modified EGII. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396 428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for a modified EGII may be produced by introducing a heterologous nucleic acid construct comprising the modified EGII coding sequence into the cells of a selected strain of the filamentous fungi.

Once the desired form of a modified egl2 nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A modified egl2 coding sequence may be inserted into a suitable vector according to well-known recombinant techniques and used to transform filamentous fungi capable of modified EGII expression. Due to the inherent degeneracy of the genetic code, other nucleic acid sequences which encode substantially the same or a functionally equivalent amino acid sequence may be used to clone and express modified EGII. Therefore it is appreciated that such substitutions in the coding region fall within the sequence variants covered by the present invention. Any and all of these sequence variants can be utilized in the same way as described herein for a parent modified EGII-encoding nucleic acid sequence.

The present invention also includes recombinant nucleic acid constructs comprising one or more of the modified EGII-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for modified egl2, or a variant, fragment or splice variant thereof: (i) in isolation; (ii) in combination with additional coding sequences; such as fusion protein or signal peptide coding sequences, where the egl2 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the modified egl2 coding sequence is a heterologous gene.

In one aspect of the present invention, a heterologous nucleic acid construct is employed to transfer a modified EGII-encoding nucleic acid sequence into a cell in vitro, with established filamentous fungal and yeast lines preferred. For long-term, high-yield production of modified EGII, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1.alpha. promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a modified EGII polypeptide. Such linkage comprises positioning of the promoter with respect to the initiation codon of the DNA sequence encoding the modified EGII polypeptide in the disclosed expression vectors. The promoter sequence contains transcription and translation control sequence which mediate the expression of the modified EGII polypeptide. Examples include the promoters from the *Aspergillus niger*, A awamori or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *T. reesei* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *T. reesei* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, and pUC100.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991. All patents, patent applications, articles and publications mentioned herein, are hereby expressly incorporated herein by reference.

Transformation of Host Cells

The invention further provides cells and cell compositions which have been genetically modified to comprise an exogenously provided a modified EGII-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

Various methods may be employed for delivering an expression vector into cells in vitro. After a suitable vector is constructed, it is used to transform strains of fungi or yeast. General methods of introducing nucleic acids into cells for expression of heterologous nucleic acid sequences are known to the ordinarily skilled artisan. Such methods include, but not limited to, electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; and the like.

Methods for introducing a heterologous nucleic acid construct (expression vector) into filamentous fungi (e.g., *T. reesei*) include, but are not limited to the use of a particle or gene gun, permeabilization of filamentous fungi cells walls prior to the transformation process (e.g., by use of high concentrations of alkali, e.g., 0.05 M to 0.4 M CaCl.sub.2 or lithium acetate), protoplast fusion or *agrobacterium* mediated transformation. An exemplary method for transformation of filamentous fungi by treatment of protoplasts or spheroplasts with polyethylene glycol and CaCl.sub.2 is described in Campbell, E. I. et al., Curr. Genet. 16:53 56, 1989 and Penttila, M. et al., Gene, 63:1122, 1988.

In addition, heterologous nucleic acid constructs comprising a modified EGII-encoding nucleic acid sequence can be transcribed in vitro, and the resulting RNA introduced into the host cell by well-known methods, e.g., by injection.

Following introduction of a heterologous nucleic acid construct comprising the coding sequence for the modified egl2, the genetically modified cells can be cultured in conventional nutrient media modified as appropriate for activating promoters, selecting transformants or amplifying expression of an EGII-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the modified EGII-encoding nucleic acid sequence found in the heterologous nucleic acid construct.

Novel and useful transformants of filamentous fungi such as *Trichoderma reesei* for use in producing cellulase compositions are contemplated. The invention includes transformants of filamentous fungi especially fungi comprising the modified egl2 coding sequence or comprising a modified form of the modified egl2 coding sequence.

Stable transformants of filamentous fungi can generally be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

Analysis for Modified EGII Nucleic Acid Coding Sequences and/or Protein Expression In order to evaluate the expression of modified EGII by a cell line that has been transformed with a modified EGII-encoding nucleic acid construct, assays can be carried out at the protein level, the RNA level or by use of functional bioassays particular to endoglucanase activity and/or production.

In one exemplary application of the modified egl2 nucleic acid and protein sequences described herein, a genetically modified strain of filamentous fungi, e.g., *Trichoderma reesei*, is engineered to produce an increased amount of modified EGII. Such genetically modified filamentous fungi would be useful to produce a cellulase product with greater increased cellulolytic capacity. In one approach, this is accomplished by introducing the coding sequence for modified egl2 into a suitable host, e.g., a filamentous fungi such as *Trichoderma reesei*.

Accordingly, the invention includes methods for expressing modified EGII in a filamentous fungus or other suitable host by introducing an expression vector containing the DNA sequence encoding modified EGII into cells of the filamentous fungus or other suitable host.

In another aspect, the invention includes methods for modifying the expression of modified EGII in a filamentous fungus or other suitable host. Such modification includes a decrease or elimination in expression, or expression of an altered form of modified EGII. An altered form of modified EGII may have an altered amino acid sequence or an altered nucleic acid sequence.

In general, assays employed to analyze the expression of modified EGII include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of modified EGII may be measured in a sample directly, for example, by assays for endoglucanase activity, expression and/or production. Such assays are described, for example, in Shoemaker, S. P. and Brown, R. D. Jr. (Biochim. Biophys. Acta, 1978, 523:133 146; Schulein (1988) and U.S. Pat. Nos. 5,246,853 and 5,475,101 each of which is expressly incorporated by reference herein. The ability of modified EGII to hydrolyze isolated soluble and insoluble substrates can be measured using assays described in Suurnakki et al. (2000) and Ortega et al. (2001). Substrates useful for assaying cellobiohydrolase, endoglucanase or β-glucosidase activities include crystalline cellulose, filter paper, phosphoric acid swollen cellulose, hydroxyethyl cellulose, carboxymethyl cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside, orthonitrophenyl glucoside, paranitrophenyl glucoside, methylumbelliferyl glycoside.

Endoglucanase activity may be determined using carboxymethyl cellulose (CMC) hydrolysis according to the procedure of Ghose, 1987, *Pure and Appl. Chem.* 59: 257-268 or Wood, T. M., and K. M. Bhat, 1988, Methods for measuring cellulase activities. Methods Enzymol. 160:87-112. Briefly, endoglucanase activity may be determined in vitro using CMC as a substrate. Appropriate dilutions of cell-free culture broth (extracellular activity) or broth containing cells that had been disrupted by ultrasound (total activity) may be assayed at 50° C. in 50 mM sodium acetate buffer (pH 4.8) containing low-viscosity CMC (10 g per liter). Reactions were terminated by heating in a boiling water bath for 5-10 min. Reducing sugars were measured using 3,5-dinitrosalicylic acid reagent with glucose as a standard. Enzyme activity (CMCase) is expressed as micromoles of reducing sugar released per minute (in international units).

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of modified EGII. The details of such methods are known to those of skill in the art and many reagents for practicing such methods are commercially available.

A purified form of modified EGII may be used to produce either monoclonal or polyclonal antibodies specific to the expressed protein for use in various immunoassays. (See, e.g., Hu et al., 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of endoglucanase proteins.

Methods For Purifying A Modified EGII

In general, a modified EGII cellulase produced in cell culture is secreted into the medium and may be purified or isolated, e.g., by removing unwanted components from the cell culture medium. However, in some cases, a modified EGII cellulase may be produced in a cellular form necessitating recovery from a cell lysate. In such cases the modified EGII cellulase is purified from the cells in which it was produced using techniques routinely employed by those of skill in the art. Examples include, but are not limited to, affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

Typically, the modified EGII cellulase is fractionated to segregate proteins having selected properties, such as binding affinity to particular binding agents, e.g., antibodies or receptors; or which have a selected molecular weight range, or range of isoelectric points.

Once expression of a modified EGII cellulase is achieved, the modified EGII cellulase thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, 1990; Scopes, 1982. The purification step(s) selected will depend, e.g., on the nature of the production process used and the particular protein produced.

Utility

The depilling treatment conditions used in the following examples are believed consistent with those generally used for depilling. When depilling takes place in a typical manufacturing process, depilling treatment time is about 15 to about 120 minutes; depilling treatment temperature is about 35° C. to about 60° C., the ratio of liquor to fabric is between about 2.5:1 and about 10:1 by weight, and the pH is about 4.0 to about 6.0. When depilling takes place in a typical laundering, the treatment time is about 10 to 60 minutes, the temperature is about 20° C. to about 70° C., the ratio of liquor to fabric is between about 2.5:1 and about 10:1 by weight, and the pH is about 7.0 to about 9.5.

The amount of treating composition used to depill depends on the concentration of active protein in the cellulase composition, the amount of cotton goods being treated, and the desired amount of depilling effect, the time of treatment and other parameters well-known to those skilled in the art. When used for depilling in a typical manufacturing process, the preferred amount of treating composition is generally between about 2,000 and about 100,000 CMC units of enzyme per kg of fabric and more preferably between about 10,000 and about 40,000 CMC units per kg of fabric. When used for depilling in a typical laundering, the preferred amount of treating composition is generally between about 200 and about 40,000 CMC units of enzyme per kg of fabric and more preferably between about 1,000 and about 10,000 CMC units per kg of fabric.

One option for controlling the action of the enzyme, which is recommended but not required, is to destroy the enzyme after treatment by heating the solution to about 70° C. for 10 minutes, by adding chemicals that destroy enzyme activity, or by immediately drying the fabric.

Methods Of Treating Cellulose Containing Fabric Using Modified EGII Cellulase Enzymes One aspect of the invention is a composition for the treatment of a textile that includes modified EGII of the present invention. In another embodiment, the present invention relates to use of the modified EGII of the invention in the bio-polishing process. Bio-Polishing is a specific treatment of the yarn surface which improves fabric quality with respect to handle and appearance. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulytic and mechanical action is required. It is also known that "super-softness" is achievable when the treatment with a cellulase is combined with a conventional treatment with softening agents. It is contemplated that use of the modified EGII of the invention for bio-polishing of cellulosic fabrics is advantageous, e.g. a more thorough polishing can be achieved. Bio-polishing may be obtained by applying the method described e.g. in WO 93/20278.

As noted above, the present invention pertains to methods for treating cellulose containing fabrics with a modified EGII cellulase enzyme. The use of the modified EGII cellulase composition of this invention provides the novel and surprising result of effecting a relatively high level of abrasion while maintaining an equivalent level of backstaining compared to prior art cellulase treatment. Because the level of abrasion acts as an indicator of the quality and effectiveness of particular cellulase treatment techniques, e.g., stonewashing or laundering, the use of the instant invention provides a surprisingly high quality textile treatment composition. In the laundering context, abrasion is sometimes referred to as color clarification, defuzzing or biopolishing.

The present invention specifically contemplates the use of modified EGII cellulase, alone or in combination with additional cellulase components, to achieve excellent abrasion when compared to enriched EGII cellulase. Additionally, naturally occurring cellulase enzymes which lack a binding domain are contemplated as within the scope of the invention. It is also contemplated that the methods of this invention will provide additional enhancements to treated cellulose containing fabric, including improvements in the feel and/or appearance of the fabric.

A. Methodology for Textile Processing With Modified EGII Cellulase Compositions

According to the present invention, the modified EGII cellulase compositions described above may be employed in the manufacture of textiles, e.g., depilling, stonewashing, etc.

Preferably, the treating composition of the instant comprises an aqueous solution which contains an effective amount of a modified EGII cellulase together with other optional ingredients including, for example, a buffer, a surfactant, and a scouring agent.

In a typical depilling treatment step during garment manufacturing, fabric or garments, water, buffer, detergents, and enzyme are added to a rotating horizontal or vertical drum jet dyer, washing machine, or other device that provides agitation and shear to the fabric. The treatment typically uses conditions in the ranges as follows:

pH 3.5-6.0 (
Liquor ratio 1:2-1:100
Temperature: 30-70° C.
Enzyme dose: 50,000-500,000 CMC U
Time: 10-60 minutes
Fabric speed: 10-200 m/minute Alternative conditions include 15 to 120 minutes at 35° C. to 60° C., at a pH of 4 to 6.5. The ratio of liquor to fabric is usually between 2.5:1 and 20:1, by weight. Optimization of treatment conditions is well within the skill of the artisan. The amount of cellulase enzyme added typically corresponds to a cellulase activity of about 1,000 to 200,000 CMC units per kilogram of fabric, based on the cellulase assay method of Ghose (1987). After treatment, the enzyme is often destroyed by heating the solution to 70° C. for 10 minutes. The fabric is removed from the machine, dried, and prepared in rolls, sometimes after additional dying. A summary of publications that further describe details of conventional cellulase treatments for depilling of cotton fabrics during manufacturing is found in U.S. Pat. No. 5,232,851, at Column 1. Specifically contemplated formulations may include proxel (1,2-benzisothiazolin) as a preservative or antioxidant in the range of 0.03-0.20%. Specifically contemplated formulations may include glycerol in the range of 10-35%.

For a depilling treatment during a laundering step, the cellulase is included in a detergent mixture with the many other ingredients. The other ingredients might include other enzymes, such as proteases, lipases, and additional cellulases, as well as surfactants, buffers, builders, bleach, anti-redeposition agents, optical brighteners, anti-oxidants (e.g. proxel), and solubilizers.

It is known in the art a "stone-washed" look (localized abrasion of the colour) in dyed fabric, especially in denim fabric or jeans, is possible either by washing the denim or jeans made from such fabric in the presence of pumice stones to provide the desired localized lightening of the colour of the fabric or by treating the fabric enzymatically, in particular with cellulolytic enzymes. The treatment with a modified EGII of the present invention may be carried out either alone such as disclosed in U.S. Pat. No. 4,832,864, together with a smaller amount of pumice than required in the traditional process, or together with perlite such as disclosed in WO 95/09225.

An effective amount of modified EGII cellulase enzyme composition is a concentration of modified EGII cellulase enzyme sufficient for its intended purpose. Thus an "effective amount" of modified EGII cellulase in the treating composition according to the present invention is that amount which will provide the desired treatment, e.g., stonewashing, depilling, softening, etc. The amount of modified EGII cellulase employed is also dependent on the equipment employed, the process parameters employed (the temperature of the modified EGII cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of modified EGII cellulase can be readily determined by the skilled artisan based on the above factors as well as the desired result. Preferably the modified EGII cellulase composition is present in a concentration of from 1-1000 ppm, more preferably 10-400 ppm and most preferably 20-100 ppm total protein.

Optionally, a buffer is employed in the treating composition such that the concentration of buffer is that which is sufficient to maintain the pH of the solution within the range wherein the employed modified EGII cellulase exhibits activity which, in turn, depends on the nature of the modified EGII cellulase employed. The exact concentration of buffer employed will depend on several factors which the skilled artisan can readily take into account. For example, in a preferred embodiment, the buffer as well as the buffer concentration are selected so as to maintain the pH of the final modified EGII cellulase solution within the pH range required for optimal cellulase activity. Preferably, buffer concentration in the stonewashing composition is about 0.001N or greater. Suitable buffers include, for example, citrate and acetate.

In addition to modified EGII cellulase and a buffer, the treating composition may optionally contain a surfactant. Preferably, the surfactant is present in a concentration in the diluted wash mediums of greater than 100 ppm, preferably from about 200-15,000 ppm. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known in the art.

In a preferred embodiment, a concentrated treating composition can be prepared for use in the methods described herein. Such concentrates would contain concentrated amounts of the modified EGII cellulase composition described above, buffer and surfactant, preferably in an aqueous solution. When so formulated, the treating concentrate can readily be diluted with water so as to quickly and accurately prepare treating compositions according to the present invention and having the requisite concentration of these additives. Preferably, such concentrates will comprise from about 0.1 to about 50 weight percent of a fungal cellulase composition described above (protein); from about 0.1 to about 80 weight percent buffer; from about 0 to about 50 weight percent surfactant; with the balance being water. When aqueous concentrates are formulated, these concentrates can be diluted so as to arrive at the requisite concentration of the components in the modified EGII cellulase solution as indicated above. As is readily apparent, such treating concentrates will permit facile formulation of the modified EGII cellulase solutions as well as permit feasible transportation of the concentration to the location where it will be used. The treating concentrate can be in any art recognized form, for example, liquid, emulsion, gel, or paste. Such forms are well known to the skilled artisan.

When a solid treating concentrate is employed, the cellulase composition may be a granule, a powder, an agglomerate or a solid disk. When granules are used, the granules are preferably formulated so as to contain a cellulase protecting agent. See, for instance, WO 91/17235 and entitled "GRANULES CONTAINING BOTH AN ENZYME AND AN ENZYME PROTECTING AGENT AND DETERGENT COMPOSITIONS CONTAINING SUCH GRANULES," which application is incorporated herein by reference in its entirety. Likewise, the granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the treating composition of the present invention as desired, including stones, pumice, fillers, solvents, enzyme activators, and other anti-redeposition agents.

The cellulose containing fabric is contacted with the treating composition containing an effective amount of the modified EGII cellulase enzyme or derivative, and thus bringing the modified EGII cellulase enzyme into proximity with the fabric. For example, if the treating composition is an aqueous solution, the fabric may be directly soaked in the solution. Similarly, where the treating composition is a concentrate, the concentrate is diluted into a water bath with the cellulose containing fabric. When the treating composition is in a solid form, for example a pre-wash gel or solid stick, the treating composition may be contacted by directly applying the composition to the fabric or to the wash liquor.

The cellulose containing fabric is incubated with the treating solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the modified EGII cellulase enzyme to react efficiently with cellulose containing fabric. The reaction conditions for modified EGII cellulase, and thus the conditions effective for the treating compositions of the present invention, are substantially similar to well known methods used with other similar cellulases. Accordingly, the conditions effective for treatment of cellulose containing fabric with a treating composition comprising a modified EGII according to the present invention are substantially similar to those in the prior art using wild-type cellulase compositions. Accordingly, it is within the skill of those in the art to maximize conditions for using the treating compositions according to the present invention.

The liquor ratios during treatment employed herein are generally an amount sufficient to achieve the desired effect in the cellulosic fabric and is dependent upon the process used. Preferably, the liquor ratios are from about 3:1 to about 100:1; more preferably from 4:1 to about 50:1, and most preferably from about 6:1 to about 20:1.

Reaction temperatures during treatment with the present treating compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase. As a result, the maximum reaction temperatures employed herein are generally about 65° C. In view of the above, reaction temperatures are generally from about 30° C. to about 65° C.; preferably, from about 35° C. to about 60° C.; and more preferably, from about 35° C. to about 55° C.

Reaction times are dependent on the specific conditions under which the treatment occurs. For example, pH, temperature and concentration of modified EGII cellulase will all effect the optimal reaction time. Generally, reaction times are from about 5 minutes to about 5 hours, and preferably from about 10 minutes to about 3 hours and, more preferably, from about 20 minutes to about 1 hour.

Cellulose containing fabrics treated in the methods described above using modified EGII cellulase compositions (i.e., treating compositions) according to the present invention show reduced redeposition of dye, enhanced depilling and enhanced abrasion as compared to the same cellulose containing fabrics treated in the same manner with an endo-enriched EGII cellulase composition.

B. Methodology for Treating Cellulose Containing Fabrics With A Detergent Composition Comprising Modified EGII Cellulase Enzyme According to the present invention, the modified EGII cellulase compositions described above may be employed as detergent composition. The detergent compositions according to the present invention are useful as pre-wash compositions, pre-soak compositions, or for detergent cleaning during the regular wash cycle. Preferably, the detergent composition of the present invention comprises an effective amount of modified EGII cellulase, and a surfactant, and optionally include other ingredients described below.

An effective amount of modified EGII cellulase employed in the detergent compositions of this invention is an amount sufficient to impart improved abrasion to cellulase containing fabrics. Preferably, the modified EGII cellulase employed is in a concentration of about 0.001% to about 25%, more preferably, about 0.02% to about 10% by weight percent of detergent.

The specific concentration of modified EGII cellulase enzyme employed in the detergent composition is preferably selected so that upon dilution into a wash medium, the concentration of modified EGII cellulase enzyme is in a range of about 0.1 to about 1000 ppm, preferably from about 0.2 ppm to about 500 ppm, and most preferably from about 0.5 ppm to about 250 ppm total protein. Thus, the specific amount of modified EGII cellulase enzyme employed in the detergent composition will depend on the extent to which the detergent will be diluted upon addition to water so as to form a wash solution.

At lower concentrations of modified EGII cellulase enzyme, i.e., concentrations of modified EGII enzyme lower than 20 ppm, the decreased backstaining or redeposition with equivalent surface fiber abrasion when compared to prior art compositions will become evident after repeated washings. At higher concentrations, i.e., concentrations of modified EGII cellulase enzymes of greater than 40 ppm, the decreased backstaining with equivalent surface fiber removal will become evident after a single wash.

The detergent compositions of the present invention may be in any art recognized form, for example, as a liquid diluent, in granules, in emulsions, in gels, or in pastes. Such forms are well known to the skilled artisan. When a solid detergent composition is employed, the modified EGII cellulase is preferably formulated as granules. Preferably, the granules can be formulated so as to additionally contain a cellulase protecting agent. See, for instance, WO 91/17235 entitled "GRANULES CONTAINING BOTH AN ENZYME AND AN ENZYME PROTECTING AGENT AND DETERGENT COMPOSITIONS CONTAINING SUCH GRANULES". Likewise, the granule can be formulated so as to contain materials to reduce the rate of dissolution of the granule into the wash medium. Such materials and granules are disclosed in U.S. Pat. No. 5,254,283 which is incorporated herein by reference in its entirety.

The modified EGII of the invention are useful in formulating various detergent compositions. A number of known compounds are suitable surfactants useful in compositions comprising the modified EGII of the invention. These include nonionic, anionic, cationic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015. The art is familiar with the different formulations which can be used as detergent compositions. In addition to typical detergent compositions, it is readily understood that the modified EGII of the present invention may be used for any purpose that native or wild-type cellulase are used. The variants of the present invention may comprise enhanced performance in a detergent composition (as compared to the wildtype). As used herein, enhanced performance in a detergent is defined as increasing cleaning of certain enzyme sensitive stains, as determined by usual evaluation after a standard wash cycle.

Modified EGII of the invention can be formulated into known powdered and liquid detergents having pH between 6.5 and 12.0 at levels of about 0.01 to about 5% (preferably 0.1% to 0.5%) by weight. These detergent compositions can also include other enzymes such as known proteases, amylases, cellulases, lipases or endoglycosidases, as well as builders and stabilizers.

The addition of modified EGII of the invention to conventional detergent compositions does not create any special use limitation. In other words, any temperature and pH suitable for the detergent is also suitable for the present compositions as long as the pH is within the above range, and the temperature is below the described modified EGII's denaturing temperature. In addition, modified EGII of the invention can be used in a detergent composition without detergents, again either alone or in combination with builders and stabilizers.

The present invention also relates to detergent compositions containing the modified EGII of the invention. The detergent compositions may additionally contain additives which are commonly used in detergent compositions. These can be selected from, but not limited to, bleaches, surfactants, builders, enzymes and bleach catalysts. See, for example, U.S. Pat. No. 6,268,169. It would be readily apparent to one of ordinary skill in the art what additives are suitable for inclusion into the compositions. The list provided herein is by no means exhaustive and should be only taken as examples of suitable additives. It will also be readily apparent to one of ordinary skill in the art to only use those additives which are compatible with the enzymes and other components in the composition, for example, surfactant.

When present, the amount of additive present in the detergent composition is from about 0.01% to about 99.9%, preferably about 1% to about 95%, more preferably about 1% to about 80%.

Animal Feed

The modified EGII of the present invention can be included in animal feed such as part of animal feed additives as described in, for example, U.S. Pat. Nos. 5,612,055; 5,314, 692; and 5,147,642.

Pulp and Paper Applications

In the papermaking pulp industry, the modified EGII of the present invention may be applied advantageously e.g. as follows:

For debarking: pretreatment with the modified EGII may degrade the cambium layer prior to debarking in mechanical drums resulting in advantageous energy savings.

For defibration: treatment of a material containing cellulosic fibers with the modified EGII prior to refining or beating may result in reduction of the energy consumption due to the hydrolysing effect of the cellulase on the interfibre surfaces. Use of the modified EGII may result in improved energy savings as compared to the use of known enzymes, since it is believed that the enzyme composition of the invention may possess a higher ability to penetrate fibre walls.

For fibre modification, i.e. improvement of fibre properties where partial hydrolysis across the fibre wall is needed which requires deeper penetrating enzymes (e.g. in order to make coarse fibers more flexible). Deep treatment of fibers has so far not been possible for high yield pulps e.g. mechanical pulps or mixtures of recycled pulps. This has been ascribed to the nature of the fibre wall structure that prevents the passage of enzyme molecules due to physical restriction of the pore matrix of the fibre wall. It is contemplated that the present endoglucanase is capable of penetrating into the fibre wall.

For drainage improvement. The drainability of papermaking pulps may be improved by treatment of the pulp with hydrolysing enzymes, e.g. cellulases. Use of the present modified EGII may be more effective, e.g. result in a higher degree of loosening bundles of strongly hydrated microfibrils in the fines fraction (consisting of fibre debris) that limits the rate of drainage by blocking hollow spaces between fibers and in the wire mesh of the paper machine. The Canadian standard freeness (CSF) increases and the Schopper-Riegler drainage index decreases when pulp in subjected to cellulase treatment, see e.g. U.S. Pat. Nos. 4,923,565 and 4,613,406.

For inter fibre bonding. Hydrolytic enzymes are applied in the manufacture of papermaking pulps for improving the inter fibre bonding. The enzymes rinse the fibre surfaces for impurities e.g. cellulosic debris, thus enhancing the area of exposed cellulose with attachment to the fibre wall, thus improving the fibre-to-fibre hydrogen binding capacity. This process is also referred to as dehornification. Paper and board produced with a cellulase containing enzyme preparation may have an improved strength or a reduced grammage, a smoother surface and an improved printability.

For enzymatic deinking. Partial hydrolysis of recycled paper during or upon pulping by use of hydrolysing enzymes such as cellulases are known to facilitate the removal and agglomeration of ink particles. Use of the present modified EGII may give a more effective loosening of ink from the surface structure due to a better penetration of the enzyme molecules into the fibrillar matrix of the fibre wall, thus softening the surface whereby ink particles are effectively loosened. The agglomeration of loosened ink particles are also improved, due to a more efficient hydrolysis of cellulosic fragments found attached to ink particles originating from the fibres.

The treatment of lignocellulosic pulp may, e.g., be performed as described in WO 91/14819, WO 91/14822, WO 92/17573 and WO 92/18688.

Degradation of Plant Material

In yet another embodiment, the present invention relates to use of the modified EGII and/or enzyme composition according to the invention for degradation of plant material e.g. cell walls.

It is contemplated that the modified EGII and/or enzyme composition of the invention is useful in the preparation of wine, fruit or vegetable juice in order to increase yield. The modified EGII according to the invention may also be applied for enzymatic hydrolysis of various plant cell-wall derived materials or waste materials, e.g. agricultural residues such as wheat-straw, corn cobs, whole corn plants, nut shells, grass, vegetable hulls, bean hulls, spent grains, sugar beet pulp, and the like. The plant material may be degraded in order to improve different kinds of processing, facilitate purification or extraction of other components like purification of beta-glucan or beta-glucan oligomers from cereals, improve the feed value, decrease the water binding capacity, improve the degradability in waste water plants, improve the conversion of e.g. grass and corn to ensilage, etc.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); Ts (tosyl); Bn (benzyl); Ph (phenyl); Ms (mesyl); Et (ethyl), Me (methyl).

deleted. See U.S. Pat. No. 5,472,864 and WO 92/17574 for techniques to delete the desired cellulases, e.g., CBHI, CBHII, EGI, and EGII. The host strain used was *T. reesei* strain RL-P37. The derivation and characterization of this strain has been published previously (Sheir-Neiss and Montenecourt, 1984). It is a cellulase over-producing strain that has been obtained as a result of several mutagenesis steps from the wild-type strain (QM6a).

For *T. reesei* Eg2 A, sequences encoding CBHI, CBHII have been inactivated by deletion or disruption using molecular genetic techniques.

For *T. reesei* EG2 B, sequencing encoding CBHI, CBHII, EGI, and EGII have been inactivated by deletion or disruption using molecular genetic techniques.

*T. reesei* EG2 A and B, were transformed with a single copy of the nucleotide sequence shown in FIG. 2 that had been placed under the control of the high efficiency promoter obtained from the CBHI encoding gene.

Construction of the EG II Expression Cassette

The egl II gene was isolated using PCR with primers designed according to the egl II nucleotide sequence published by Saloheimo, M. et al. 1988 containing eg II gene specific sequences. Restriction sites were added to egl II to allow insertion into vector pTrex3 (see U.S. Pat. No. 6,426, 410). Using the forward primer, a Sac II site was added. Also, the last 10 nucleotides of the CBH1 promoter, directly preceding the CBH1 signal sequence, were added as this can increase expression. Using the reverse primer, an Asc I site was added. The sequence of the forward and reverse primer are shown below:

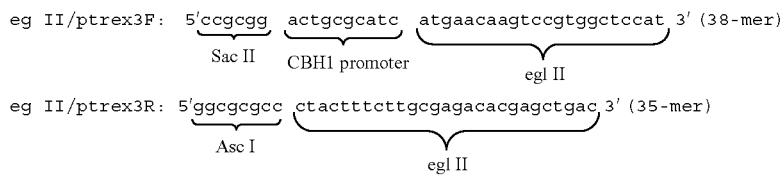

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

EGII Expression

This example illustrates construction of host cells and expression of the modified EGII cellulase.

A strain that is low in cellulolytic activities was desired for biofinishing and denim washing applications. New strains were constructed with some or all of the major cellulases The PCR mix contained the following components: Forward primer (10 μM) 1 μL; Reverse primer (10 μM) 1 μL; DNA (500 ng/μL) 1 μL; dNTPs (10 mM) 1 μL; 10× Herculase buffer; 5 μL and Herculase DNA polymerase; 0.5 μL (Stratagene Cat. # 60026) and deionized water up to a total volume of 50 μL.

The PCR protocol was as follows: Initial denaturation for 60 sec. at 94° C., 23 cycles of denaturation, annealing and extension of 30 sec at 94° C.; 30 sec at 50° C.; 90 sec at 72° C., respectively, and a final extension step of 5 min at 72° C.

Figure 5:
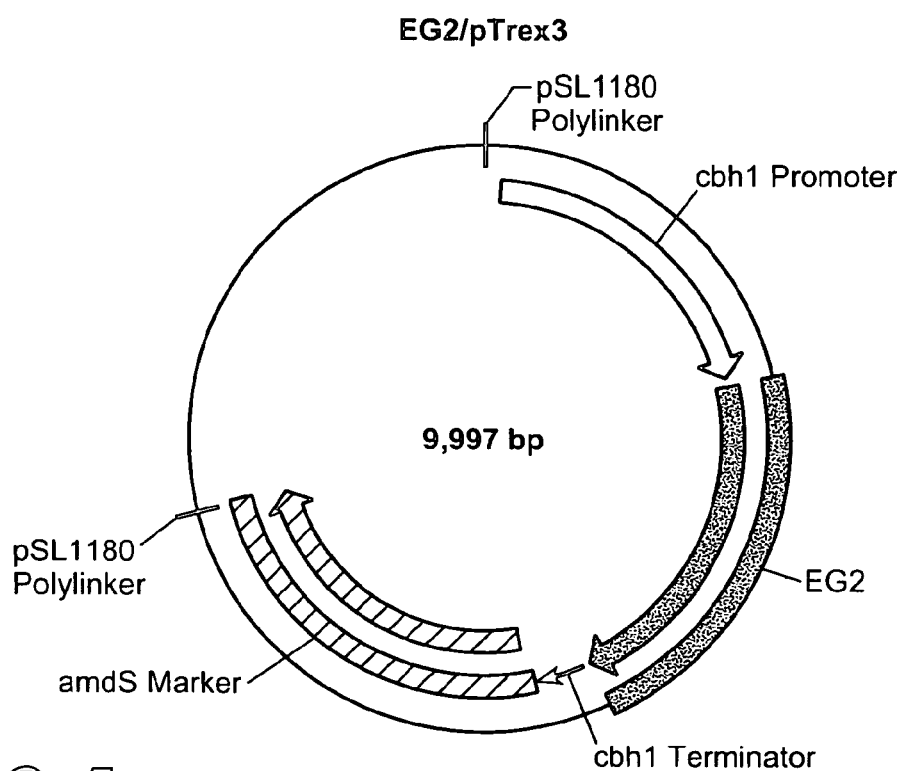
Figure 6:
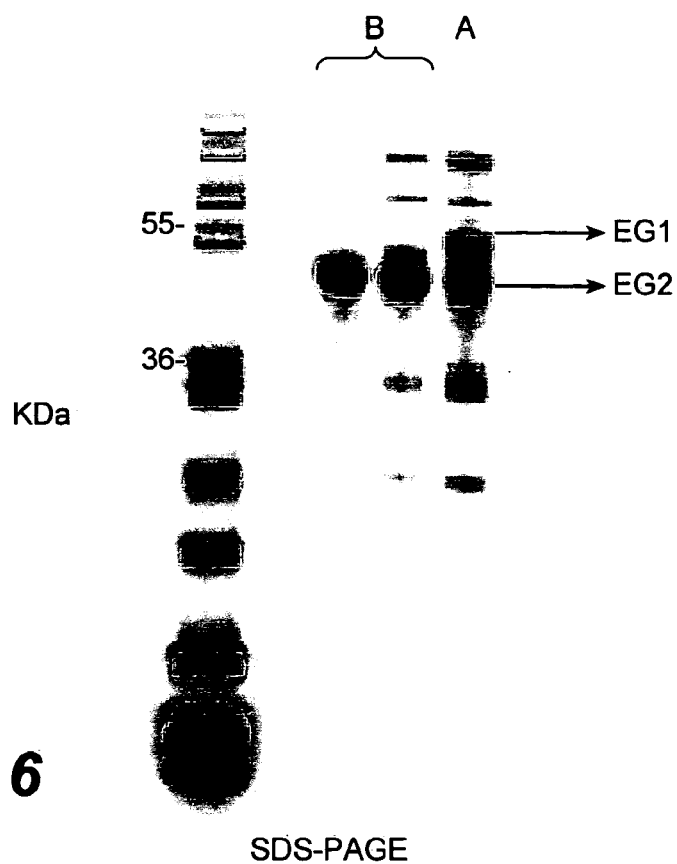
FIG. 6 is an SDS-PAGE of concentrated supernatants derived from $T.$ $reesei$ EG2 strains A and B (described in Examples 1 and 2).

The PCR fragments were analyzed by electrophoresis in 1% agarose. Fragments of the expected size were isolated using the Gel-Extraction Purification Kit (Qiagene Cat. No. 28706). The PCR fragments were cloned into pTrex3 forming pEG2/pTrex 3 (see FIGS. 5 and 6) and transformed into *E. coli* DH5alpha Max Efficiency cells (Invitrogen Cat. No. 18258012). The nucleotide sequence of the inserted DNA was determined (see FIG. 2). pEG2/pTrex 3 has the following sequence wherein upper case letters denote pTrex3 plasmid nucleotides, the lower case denote EG2 nucleotides:

```
AAGCTTACTA GTACTTCTCG AGCTCTGTAC ATGTCCGGTC GCGACGTACG   50
CGTATCGATG GCGCCAGCTG CAGGCGGCCG CCTGCAGCCA CTTGCAGTCC  100
CGTGGAATTC TCACGGTGAA TGTAGGCCTT TTGTAGGGTA GGAATTGTCA  150
CTCAAGCACC CCCAACCTCC ATTACGCCTC CCCCATAGAG TTCCCAATCA  200
GTGAGTCATG GCACTGTTCT CAAATAGATT GGGGAGAAGT TGACTTCCGC  250
CCAGAGCTGA AGGTCGCACA ACCGCATGAT ATAGGGTCGG CAACGGCAAA  300
AAAGCACGTG GCTCACCGAA AGCAAGATG TTTGCGATCT AACATCCAGG  350
AACCTGGATA CATCCATCAT CACGCACGAC CACTTTGATC TGCTGGTAAA  400
CTCGTATTCG CCCTAAACCG AAGTGCGTGG TAAATCTACA CGTGGGCCCC  450
TTTCGGTATA CTGCGTGTGT CTTCTCTAGG TGCCATTCTT TTCCCTTCCT  500
CTAGTGTTGA ATTGTTTGTG TTGGAGTCCG AGCTGTAACT ACCTCTGAAT  550
CTCTGGAGAA TGGTGGACTA ACGACTACCG TGCACCTGCA TCATGTATAT  600
AATAGTGATC CTGAGAAGGG GGGTTTGGAG CAATGTGGGA CTTTGATGGT  650
CATCAAACAA AGAACGAAGA CGCCTCTTTT GCAAAGTTTT GTTTCGGCTA  700
CGGTGAAGAA CTGGATACTT GTTGTGTCTT CTGTGTATTT TTGTGGCAAC  750
AAGAGGCCAG AGACAATCTA TTCAAACACC AAGCTTGCTC TTTTGAGCTA  800
CAAGAACCTG TGGGTATAT ATCTAGAGTT GTGAAGTCGG TAATCCCGCT  850
GTATAGTAAT ACGAGTCGCA TCTAAATACT CCGAAGCTGC TGCGAACCCG  900
GAGAATCGAG ATGTGCTGGA AAGCTTCTAG CGAGCGGCTA AATTAGCATG  950
AAAGGCTATG AGAAATTCTG GAGACGGCTT GTTGAATCAT GGCGTTCCAT 1000
TCTTCGACAA GCAAAGCGTT CCGTCGCAGT AGCAGGCACT CATTCCCGAA 1050
AAAACTCGGA GATTCCTAAG TAGCGATGGA ACCGGAATAA TATAATAGGC 1100
AATACATTGA GTTGCCTCGA CGGTTGCAAT GCAGGGGTAC TGAGCTTGGA 1150
CATAACTGTT CCGTACCCCA CCTCTTCTCA ACCTTTGGCG TTTCCCTGAT 1200
TCAGCGTACC CGTACAAGTC GTAATCACTA TTAACCCAGA CTGACCGGAC 1250
GTGTTTTGCC CTTCATTTGG AGAAATAATG TCATTGCGAT GTGTAATTTG 1300
CCTGCTTGAC CGACTGGGGC TGTTCGAAGC CCGAATGTAG GATTGTTATC 1350
CGAACTCTGC TCGTAGAGGC ATGTTGTGAA TCTGTGTCGG GCAGGACACG 1400
CCTCGAAGGT TCACGGCAAG GGAAACCACC GATAGCAGTG TCTAGTAGCA 1450
ACCTGTAAAG CCGCAATGCA GCATCACTGG AAAATACAAA CCAATGGCTA 1500
AAAGTACATA AGTTAATGCC TAAAGAAGTC ATATACCAGC GGCTAATAAT 1550
TGTACAATCA AGTGGCTAAA CGTACCGTAA TTTGCCAACG GCTTGTGGGG 1600
TTGCAGAAGC AACGGCAAAG CCCCACTTCC CCACGTTTGT TTCTTCACTC 1650
AGTCCAATCT CAGCTGGTGA TCCCCCAATT GGGTCGCTTG TTTGTTCCGG 1700
TGAAGTGAAA AAGACAGAG GTAAGAATGT CTGACTCGGA GCGTTTTGCA 1750
TACAACCAAG GGCAGTGATG GAAGACAGTG AAATGTTGAC ATTCAAGGAG 1800
TATTTAGCCA GGGATGCTTG AGTGTATCGT GTAAGGAGGT TTGTCTGCCG 1850
ATACGACGAA TACTGTATAG TCACTTCTGA TGAAGTGGTC CATATTGAAA 1900
TGTAAAGTCG GCACTGAACA GGCAAAAGAT TGAGTTGAAA CTGCCTAAGA 1950
TCTCGGGCCC TCGGGCCTTC GGCCTTTGGG TGTACATGTT TGTGCTCCGG 2000
GCAAATGCAA AGTGTGGTAG GATCGAACAC ACTGCTGCCT TTACCAAGCA 2050
```

```
GCTGAGGGTA TGTGATAGGC AAATGTTCAG GGGCCACTGC ATGGTTTCGA    2100
ATAGAAAGAG AAGCTTAGCC AAGAACAATA GCCGATAAAG ATAGCCTCAT    2150
TAAACGGAAT GAGCTAGTAG GCAAAGTCAG CGAATGTGTA TATATAAAGG    2200
TTCGAGGTCC GTGCCTCCCT CATGCTCTCC CCATCTACTC ATCAACTCAG    2250
ATCCTCCAGG AGACTTGTAC ACCATCTTTT GAGGCACAGA AACCCAATAG    2300
TCAACCGCGG ACTGCGCATC atgaacaagt ccgtggctcc attgctgctt    2350
gcagcgtcca tactatatgg cggcgccgct gcacagcaga ctgtctgggg    2400
ccagtgtgga ggtattggtt ggagcggacc tacgaattgt gctcctggct    2450
cagcttgttc gaccctcaat ccttattatg cgcaatgtat tccgggagcc    2500
actactatca ccacttcgac ccggccacca tccggtccaa ccaccaccac    2550
cagggctacc tcaacaagct catcaactcc acccacgagc tctgggtcc    2600
gatttgccgg cgttaacatc gcgggttttg actttggctg taccacagag    2650
tgagtaccct tgtttcctgg tgttgctggc tgaaaagttg ggcgggtata    2700
cagcgatgcg gactgcaaga acaccgccgg tccgccacca tcaagatgtg    2750
ggtggtaagc ggcggtgttt tgtacaacta cctgacagct cactcaggaa    2800
ctgagaatta atggaagtct tgttacagtg gcacttgcgt tacctcgaag    2850
gtttatcctc cgttgaagaa cttcaccggc tcaaacaact accccgatgg    2900
catcggccag atgcagcact tcgtcaacga cgacgggatg actattttcc    2950
gcttacctgt cggatggcag tacctcgtca acaacaattt gggcggcaat    3000
cttgattcca cgagcatttc caagtatgat cagcttgttc aggggtgcct    3050
gtctctgggc gcatactgca tcgtcgacat ccacaattat gctcgatgga    3100
acggtgggat cattggtcag ggcggcccta ctaatgctca attcacgagc    3150
ctttggtcgc agttggcatc aaagtacgca tctcagtcga gggtgtggtt    3200
cggcatcatg aatgagcccc acgacgtgaa catcaacacc tgggctgcca    3250
cggtccaaga ggttgtaacc gcaatccgca acgctggtgc tacgtcgcaa    3300
ttcatctctt tgcctggaaa tgattggcaa tctgctgggg ctttcatatc    3350
cgatggcagt gcagccgccc tgtctcaagt cacgaacccg gatgggtcaa    3400
caacgaatct gattttttgac gtgcacaaat acttggactc agacaactcc    3450
ggtactcacg ccgaatgtac tacaaataac attgacggcg ccttttctcc    3500
gcttgccact tggctccgac agaacaatcg ccaggctatc ctgacagaaa    3550
ccggtggtgg caacgttcag tcctgcatac aagacatgtg ccagcaaatc    3600
caatatctca accagaactc agatgtctat cttggctatg ttggttgggg    3650
tgccggatca tttgatagca cgtatgtcct gacggaaaca ccgactggca    3700
gtggtaactc atgacggac acatccttgg tcagctcgtg tctcgcaaga    3750
aagtagGCG CGCCGCGCGC CAGCTCCGTG CGAAAGCCTG ACGCACCGGT    3800
AGATTCTTGG TGAGCCCGTA TCATGACGGC GGCGGGAGCT ACATGGCCCC    3850
GGGTGATTTA TTTTTTTTGT ATCTACTTCT GACCCTTTTC AAATATACGG    3900
TCAACTCATC TTTCACTGGA GATGCGGCCT GCTTGGTATT GCGATGTTGT    3950
CAGCTTGGCA AATTGTGGCT TTCGAAAACA CAAAACGATT CCTTAGTAGC    4000
CATGCATTTT AAGATAACGG AATAGAAGAA AGAGGAAATT AAAAAAAAAA    4050
```

```
AAAAAACAAA CATCCCGTTC ATAACCCGTA GAATCGCCGC TCTTCGTGTA 4100

TCCCAGTACC AGTTTATTTT GAATAGCTCG CCCGCTGGAG AGCATCCTGA 4150

ATGCAAGTAA CAACCGTAGA GGCTGACACG GCAGGTGTTG CTAGGGAGCG 4200

TCGTGTTCTA CAAGGCCAGA CGTCTTCGCG GTTGATATAT ATGTATGTTT 4250

GACTGCAGGC TGCTCAGCGA CGACAGTCAA GTTCGCCCTC GCTGCTTGTG 4300

CAATAATCGC AGTGGGGAAG CCACACCGTG ACTCCCATCT TTCAGTAAAG 4350

CTCTGTTGGT GTTTATCAGC AATACACGTA ATTTAAACTC GTTAGCATGG 4400

GGCTGATAGC TTAATTACCG TTTACCAGTG CCATGGTTCT GCAGCTTTCC 4450

TTGGCCCGTA AAATTCGGCG AAGCCAGCCA ATCACCAGCT AGGCACCAGC 4500

TAAACCCTAT AATTAGTCTC TTATCAACAC CATCCGCTCC CCCGGGATCA 4550

ATGAGGAGAA TGAGGGGGAT GCGGGGCTAA AGAAGCCTAC ATAACCCTCA 4600

TGCCAACTCC CAGTTTACAC TCGTCGAGCC AACATCCTGA CTATAAGCTA 4650

ACACAGAATG CCTCAATCCT GGGAAGAACT GGCCGCTGAT AAGCGCGCCC 4700

GCCTCGCAAA AACCATCCCT GATGAATGGA AAGTCCAGAC GCTGCCTGCG 4750

GAAGACAGCG TTATTGATTT CCCAAAGAAA TCGGGGATCC TTTCAGAGGC 4800

CGAACTGAAG ATCACAGAGG CCTCCGCTGC AGATCTTGTG TCCAAGCTGG 4850

CGGCCGGAGA GTTGACCTCG GTGGAAGTTA CGCTAGCATT CTGTAAACGG 4900

GCAGCAATCG CCCAGCAGTT AGTAGGGTCC CCTCTACCTC TCAGGGAGAT 4950

GTAACAACGC CACCTTATGG GACTATCAAG CTGACGCTGG CTTCTGTGCA 5000

GACAAACTGC GCCCACGAGT TCTTCCCTGA CGCCGCTCTC GCGCAGGCAA 5050

GGGAACTCGA TGAATACTAC GCAAAGCACA AGAGACCCGT TGGTCCACTC 5100

CATGGCCTCC CCATCTCTCT CAAAGACCAG CTTCGAGTCA AGTACACCG 5150

TTGCCCCTAA GTCGTTAGAT GTCCCTTTTT GTCAGCTAAC ATATGCCACC 5200

AGGGCTACGA AACATCAATG GCTACATCT CATGGCTAAA CAAGTACGAC 5250

GAAGGGGACT CGGTTCTGAC AACCATGCTC CGCAAAGCCG GTGCCGTCTT 5300

CTACGTCAAG ACCTCTGTCC CGCAGACCCT GATGGTCTGC GAGACAGTCA 5350

ACAACATCAT CGGGCGCACC GTCAACCCAC GCAACAAGAA CTGGTCGTGC 5400

GGCGGCAGTT CTGGTGGTGA GGGTGCGATC GTTGGGATTC GTGGTGGCGT 5450

CATCGGTGTA GGAACGGATA TCGGTGGCTC GATTCGAGTG CCGGCCGCGT 5500

TCAACTTCCT GTACGGTCTA AGGCCGAGTC ATGGGCGGCT GCCGTATGCA 5550

AAGATGGCGA ACAGCATGGA GGGTCAGGAG ACGGTGCACA GCGTTGTCGG 5600

GCCGATTACG CACTCTGTTG AGGGTGAGTC CTTCGCCTCT TCCTTCTTTT 5650

CCTGCTCTAT ACCAGGCCTC CACTGTCCTC CTTTCTTGCT TTTTATACTA 5700

TATACGAGAC CGGCAGTCAC TGATGAAGTA TGTTAGACCT CCGCCTCTTC 5750

ACCAAATCCG TCCTCGGTCA GGAGCCATGG AAATACGACT CCAAGGTCAT 5800

CCCCATGCCC TGGCGCCAGT CCGAGTCGGA CATTATTGCC TCCAAGATCA 5850

AGAACGGCGG GCTCAATATC GGCTACTACA ACTTCGACGG CAATGTCCTT 5900

CCACACCCTC CTATCCTGCG CGGCGTGGAA ACCACCGTCG CCGCACTCGC 5950

CAAAGCCGGT CACACCGTGA CCCCGTGGAC GCCATACAAG CACGATTTCG 6000

GCCACGATCT CATCTCCCAT ATCTACGCGG CTGACGGCAG CGCCGACGTA 6050

ATGCGCGATA TCAGTGCATC CGGCGAGCCG GCGATTCCAA ATATCAAAGA 6100
```

```
CCTACTGAAC CCGAACATCA AAGCTGTTAA CATGAACGAG CTCTGGGACA    6150

CGCATCTCCA GAAGTGGAAT TACCAGATGG AGTACCTTGA GAAATGGCGG    6200

GAGGCTGAAG AAAAGGCCGG GAAGGAACTG GACGCCATCA TCGCGCCGAT    6250

TACGCCTACC GCTGCGGTAC GGCATGACCA GTTCCGGTAC TATGGGTATG    6300

CCTCTGTGAT CAACCTGCTG GATTTCACGA GCGTGGTTGT TCCGGTTACC    6350

TTTGCGGATA AGAACATCGA TAAGAAGAAT GAGAGTTTCA AGGCGGTTAG    6400

TGAGCTTGAT GCCCTCGTGC AGGAAGAGTA TGATCCGGAG GCGTACCATG    6450

GGGCACCGGT TGCAGTGCAG GTTATCGGAC GGAGACTCAG TGAAGAGAGG    6500

ACGTTGGCGA TTGCAGAGGA AGTGGGGAAG TTGCTGGGAA ATGTGGTGAC    6550

TCCATAGCTA ATAAGTGTCA GATAGCAATT TGCACAAGAA ATCAATACCA    6600

GCAACTGTAA ATAAGCGCTG AAGTGACCAT GCCATGCTAC GAAAGAGCAG    6650

AAAAAAACCT GCCGTAGAAC CGAAGAGATA TGACACGCTT CCATCTCTCA    6700

AAGGAAGAAT CCCTTCAGGG TTGCGTTTCC AGTCTAGACA CGTATAACGG    6750

CACAAGTGTC TCTCACCAAA TGGGTTATAT CTCAAATGTG ATCTAAGGAT    6800

GGAAAGCCCA GAATATCGAT CGCGCGCAGA TCCATATATA GGGCCCGGGT    6850

TATAATTACC TCAGGTCGAC GTCCCATGGC CATTCGAATT CGTAATCATG    6900

GTCATAGCTG TTTCCTGTGT GAAATTGTTA TCCGCTCACA ATTCCACACA    6950

ACATACGAGC CGGAAGCATA AAGTGTAAAG CCTGGGGTGC CTAATGAGTG    7000

AGCTAACTCA CATTAATTGC GTTGCGCTCA CTGCCCGCTT TCCAGTCGGG    7050

AAACCTGTCG TGCCAGCTGC ATTAATGAAT CGGCCAACGC GCGGGGAGAG    7100

GCGGTTTGCG TATTGGGCGC TCTTCCGCTT CCTCGCTCAC TGACTCGCTG    7150

CGCTCGGTCG TTCGGCTGCG GCGAGCGGTA TCAGCTCACT CAAAGGCGGT    7200

AATACGGTTA TCCACAGAAT CAGGGGATAA CGCAGGAAAG AACATGTGAG    7250

CAAAAGGCCA GCAAAAGGCC AGGAACCGTA AAAAGGCCGC GTTGCTGGCG    7300

TTTTTCCATA GGCTCCGCCC CCCTGACGAG CATCACAAAA ATCGACGCTC    7350

AAGTCAGAGG TGGCGAAACC CGACAGGACT ATAAAGATAC CAGGCGTTTC    7400

CCCCTGGAAG CTCCCTCGTG CGCTCTCCTG TTCCGACCCT GCCGCTTACC    7450

GGATACCTGT CCGCCTTTCT CCCTTCGGGA AGCGTGGCGC TTTCTCATAG    7500

CTCACGCTGT AGGTATCTCA GTTCGGTGTA GGTCGTTCGC TCCAAGCTGG    7550

GCTGTGTGCA CGAACCCCCC GTTCAGCCCG ACCGCTGCGC CTTATCCGGT    7600

AACTATCGTC TTGAGTCCAA CCCGGTAAGA CACGACTTAT CGCCACTGGC    7650

AGCAGCCACT GGTAACAGGA TTAGCAGAGC GAGGTATGTA GGCGGTGCTA    7700

CAGAGTTCTT GAAGTGGTGG CCTAACTACG GCTACACTAG AAGAACAGTA    7750

TTTGGTATCT GCGCTCTGCT GAAGCCAGTT ACCTTCGGAA AAAGAGTTGG    7800

TAGCTCTTGA TCCGGCAAAC AAACCACCGC TGGTAGCGGT GGTTTTTTTG    7850

TTTGCAAGCA GCAGATTACG CGCAGAAAAA AAGGATCTCA AGAAGATCCT    7900

TTGATCTTTT CTACGGGGTC TGACGCTCAG TGGAACGAAA ACTCACGTTA    7950

AGGGATTTTG GTCATGAGAT TATCAAAAAG GATCTTCACC TAGATCCTTT    8000

TAAATTAAAA ATGAAGTTTT AAATCAATCT AAAGTATATA TGAGTAAACT    8050

TGGTCTGACA GTTACCAATG CTTAATCAGT GAGGCACCTA TCTCAGCGAT    8100
```

```
                              -continued
CTGTCTATTT CGTTCATCCA TAGTTGCCTG ACTCCCCGTC GTGTAGATAA 8150

CTACGATACG GGAGGGCTTA CCATCTGGCC CCAGTGCTGC AATGATACCG 8200

CGAGACCCAC GCTCACCGGC TCCAGATTTA TCAGCAATAA ACCAGCCAGC 8250

CGGAAGGGCC GAGCGCAGAA GTGGTCCTGC AACTTTATCC GCCTCCATCC 8300

AGTCTATTAA TTGTTGCCGG GAAGCTAGAG TAAGTAGTTC GCCAGTTAAT 8350

AGTTTGCGCA ACGTTGTTGC CATTGCTACA GGCATCGTGG TGTCACGCTC 8400

GTCGTTTGGT ATGGCTTCAT TCAGCTCCGG TTCCCAACGA TCAAGGCGAG 8450

TTACATGTAC CCCCATGTTG TGCAAAAAAG CGGTTAGCTC CTTCGGTCCT 8500

CCGATCGTTG TCAGAAGTAA GTTGGCCGCA GTGTTATCAC TCATGGTTAT 8550

GGCAGCACTG CATAATTCTC TTACTGTCAT GCCATCCGTA AGATGCTTTT 8600

CTGTGACTGG TGAGTACTCA ACCAAGTCAT TCTGAGAATA GTGTATGCCG 8650

CGACCGAGTT GCTCTTGCCC GGCGTCAATA CGGGATAATA CCGCGCCACA 8700

TAGCAGAACT TTAAAAGTGC TCATCATTGG AAAACGTTCT TCGGGGCGAA 8750

AACTCTCAAG GATCTTACCG CTGTTGAGAT CCAGTTCGAT GTAACCCACT 8800

CGTGCACCCA ACTGATCTTC AGCATCTTTT ACTTTCACCA GCGTTTCTGG 8850

GTGAGCAAAA ACAGGAAGGC AAAATGCCGC AAAAAAGGGA ATAAGGGCGA 8900

CACGGAAATG TTGAATACTC ATACTCTTCC TTTTTCAATA TTATTGAAGC 8950

ATTTATCAGG GTTATTGTCT CATGAGCGGA TACATATTTG AATGTATTTA 9000

GAAAAATAAA CAAATAGGGG TTCCGCGCAC ATTTCCCCGA AAAGTGCCAC 9050

CTGACGTCTA AGAAACCATT ATTATCATGA CATTAACCTA TAAAAATAGG 9100

CGTATCACGA GGCCCTTTCG TCTCGCGCGT TTCGGTGATG ACGGTGAAAA 9150

CCTCTGACAC ATGCAGCTCC CGGAGACGGT CACAGCTTGT CTGTAAGCGG 9200

ATGCCGGGAG CAGACAAGCC CGTCAGGGCG CGTCAGCGGG TGTTGGCGGG 9250

TGTCGGGGCT GGCTTAACTA TGCGGCATCA GAGCAGATTG TACTGAGAGT 9300

GCACCATAAA ATTGTAAACG TTAATATTTT GTTAAAATTC GCGTTAAATT 9350

TTTGTTAAAT CAGCTCATTT TTTAACCAAT AGGCCGAAAT CGGCAAAATC 9400

CCTTATAAAT CAAAAGAATA GCCCGAGATA GGGTTGAGTG TTGTTCCAGT 9450

TTGGAACAAG AGTCCACTAT TAAAGAACGT GGACTCCAAC GTCAAAGGGC 9500

GAAAAACCGT CTATCAGGGC GATGGCCCAC TACGTGAACC ATCACCCAAA 9550

TCAAGTTTTT TGGGGTCGAG GTGCCGTAAA GCACTAAATC GGAACCCTAA 9600

AGGGAGCCCC CGATTTAGAG CTTGACGGGG AAAGCCGGCG AACGTGGCGA 9650

GAAAGGAAGG GAAGAAAGCG AAAGGAGCGG GCGCTAGGGC GCTGGCAAGT 9700

GTAGCGGTCA CGCTGCGCGT AACCACCACA CCCGCCGCGC TTAATGCGCC 9750

GCTACAGGGC GCGTACTATG GTTGCTTTGA CGTATGCGGT GTGAAATACC 9800

GCACAGATGC GTAAGGAGAA AATACCGCAT CAGGCGCCAT TCGCCATTCA 9850

GGCTGCGCAA CTGTTGGGAA GGGCGATCGG TGCGGGCCTC TTCGCTATTA 9900

CGCCAGCTGG CGAAAGGGGG ATGTGCTGCA AGGCGATTAA GTTGGGTAAC 9950

GCCAGGGTTT TCCCAGTCAC GACGTTGTAA AACGACGGCC AGTGCCC    9997
```

The expression vector containing the *T. reesei* egl II gene, pEGII/ptrex3 (see FIGS. 5 and 6) was digested to confirm the correct insert size. Plasmid DNA from one correct clone was digested with XbaI to release the expression cassette including the cbhl promoter-egl II-cbhl terminator-amdS. This 6.0 kb cassette was purified by agarose extraction and transformed into *T. reesei* to yield a strain referred to as Eg2 B.

Methods for transformation of *T. reesei* with exogenously added plasmid DNA have been published (Penttila et al., 1986; Gruber et al., 1990; Smith et al., 1991). Stable transformants arise by integration of plasmid DNA into the chromosomes of the host. Integration can be at sites in the genome that have homology with a region of the plasmid DNA or can be at non-homologous sites.

Example 2

Biochemical Characterization of EG2 Enriched *T. reesei* Products

The following example details how the EGII was recovered and characterized.

*T. reesei* strain EG2 B produced a modified EG2 was grown in fermentors, using methods known in the art, the supernatent was recovered and concentrated using methods known to those skilled in the art. The supernatent product, modified EG2 (EG2 B), and IndiAge® Max L (EG2 A) were concentrated so that they would have the same amount of EG2 protein. IndiAge® Max L and modified EG2 were formulated with either 13% sorbitol, 1.35% sodium benzoate, or 13% glycerol, 1.35% sodium benzoate.

IndiAge® Max L was formulated to 124 g/L protein (scatter-corrected A 280 nm).

Densitometry (Amersham Biosciences) results from an SDS-PAGE gel indicated that the major component of this supernatent was about 35% EG1 and 50% EG2 protein. Modified EG2 was formulated to 78 g/L protein (Scatter-corrected A 280 nm). Densitometry (Amersham Biosciences) results showed that this product contained 96% EG2 protein. When concentrated to contain the same amount of EG2 protein, IndiAge® Max L and modified EG2 were found to have similar endoglucanase activity based on a CMC/DNS assay. IndiAge® Max L and modified EG2 were dosed on CMC activity in the biofinishing and denim washing application tests (described below).

Protein assay—Scatter-corrected A 280 nm is based on the intrinsic absorption of proteins due to the presence of aromatic amino acids in their composition (mainly tyrosine and tryptophan). A more accurate determination if with the absorbance is corrected for scattering due to the possible presence of interfering substances in the sample.

Use a clean 3 mL quartz cuvette, add 3 mL of MilliQ water. Autozero a UV/Vis Spectrophotometer (Perkin Elmer Lambda 35 or Cary3) with a data Interval 1 nm, scanning speed 120 nm/min, and slit 0.5 nm). Dilute sample such as the addition of 100 uL onto 3 mL of water will give an A280 that fall between 0.04 and 0.2 absorbance units. Add 100 uL of diluted sample and mix. Scan from 650 to 250 wavelength.

Correction by scattering was done by extrapolating the linear relationship between the log of the observed absorbance vs. the log of the wavelength.

Concentrations were calculated by considering a molar absortivity of 0.94 AU $M^{-1}$ $cm^{-1}$ (calculated by Vector NTI software based on EG2 sequence). Spectra were run by triplicate at different dilutions.

Densitometry analysis was done using an Image Scanner instrument (Amersham Biosciences) and the 1D Gel Analysis done using ImageQuant TL v2005 (Amersham Biosciences) software.

Example 3

Biopolishing Performance

This example describes differences in surface fiber removal and depilling that are found when cellulase products with a different composition are being used in finishing fabrics that contain cellulosic fibers. Specifically, this example describes that a modified EG II endoglucanase has an improved surface fiber removal compared to the EG II endo-enriched cellulase (IndiAge® MAX L, available from Genencor, Palo Alto, Calif.).

These cellulase compositions were tested for their ability to remove surface fibers and pills from fabrics containing cellulosic fibers.

Specifically, fabric samples (Brushed cotton knit; a 100% cotton interlock manufactured by Intertex LLC (Garden Grove, Calif.) that is dyed with reactive royal blue and one side of the fabric is brushed) were treated in a Thies mini-soft (3 kg) jet dyer (Thies, Coesfeld Germany; on the Web at thiestextilmaschinen.de) under the following conditions:

Buffer pH 5: sodium citrate di-hydrate (1 g/l) and citric acid monohydrate (0.8 g/l)
Liquor: 30 l water
Fabric: 3 kg±0.1 kg
Liquor ratio 1:10 (1 kg fabric in 10 liter water)
Temperature: 60° C.
Enzyme dose: 113,176 or 213,579 or 318,830 CMC Units *
Time: 30 minutes
Fabric speed: 100 m/minute Following the enzyme treatment the enzyme was inactivated by adding 1 g sodium carbonate/l, raising the pH to a value of >9 at 60° C. for 5 minutes. The fabric was rinsed twice with 30 l water and dried in a household dryer.

The amount of pills and fabric surface fibers present on the treated fabric were quantified using at least one of two methods (usually both). The first method used a Videometer, VideometerLab 2 Image analyser system (Videometer, Horsholm Denmark; on the Web at videometer.com). The image analyzer is equipped with software that quantifies the amount of surface fibers and pills on the fabric. Alternatively the amount of fabric surface fuzz can be quantified visually (e.g. ASTM test method D3512-02).

Figure 7:
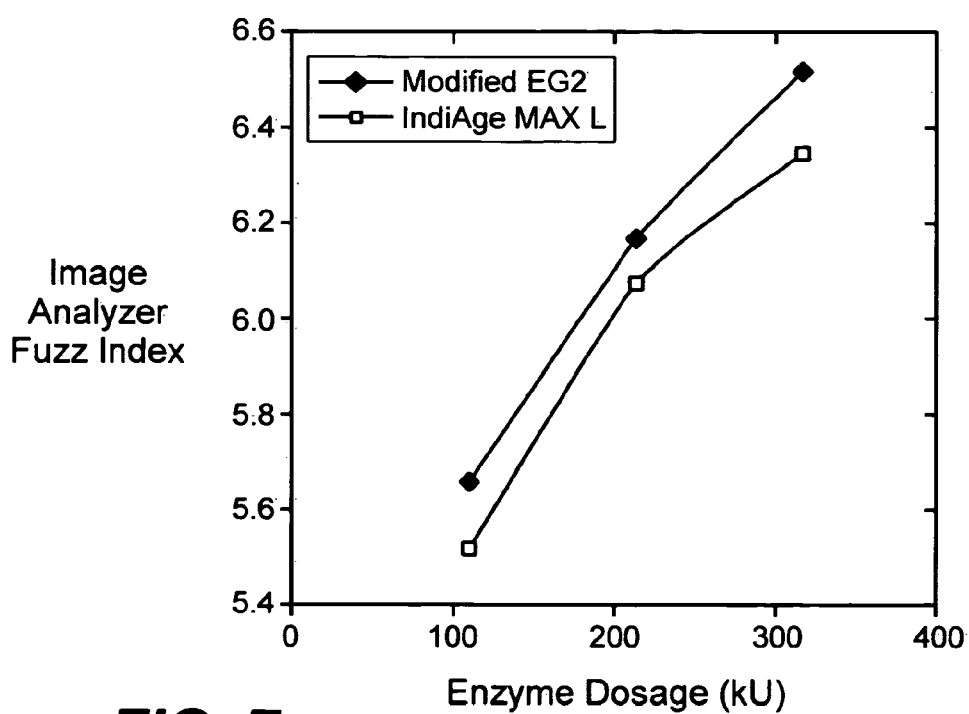
FIG. 7 is a graphical representation of the results provided in Table 1 of the surface fiber quantification for depilling following enzymatic treatment.
Figure 9:
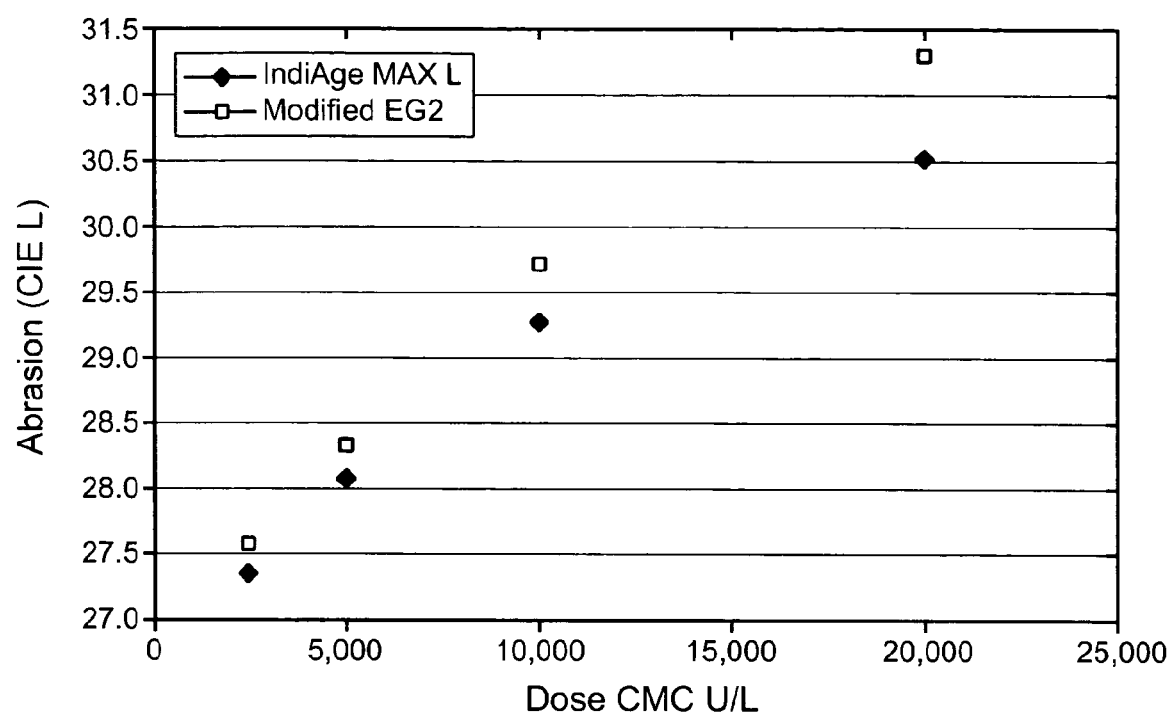
FIG. 9 is a graphical representation of the results provided in Table 2 of fabric abrasion.

Results from the Videometer are presented below in Table 1. See also FIG. 7. FIG. 8 are pictures of the fabrics that have been treated with the same activity of cellulase enzyme as used for visual assessment.

TABLE 1

Fabric surface fiber quantification

| Cellulase Enzyme Dose (U) | IndiAge ® MAX | Modified EGII |
|---|---|---|
| 113,176 | 5.51 | 5.66 |
| 213,579 | 6.07 | 6.16 |
| 318,830 | 6.34 | 6.52 |

The values in the table express the amount of fabric surface fibers. The higher the number, the lower the amount of fabric surface fibers and pills.

These results indicate that modified EGII component cellulase removes pills and fabric surface fibers (fuzz) more effectively than IndiAge® MAX cellulase when the same amount of activity units are dosed in a biofinishing process as described above.

Example 4

Denim Abrasion Performance

This example illustrates the improved denim finishing properties of a modified EGII textile processing composition. An increase in abrasion level is obtained when treating denim fabric with the modified EGII textile processing composition compared to IndiAge Max L under the following conditions.

IndiAge® Max L and modified Eg2 were compared on denim biostone washing in a high shear washing machine.

Denim legs were treated with the IndiAge Max L and modified EG2 at dosages of 2,500. 5,000, 10,000, and 20,000 CMC U/L under the following conditions:
  Equipment: Unimac (50 lb lab scale front loading washer)
  Denim substrates: 12 desized (6-sulfur bottom/indigo dyed denim legs +6-100% indigo dyed denim legs as ballasts) from Cone Mill
  Enzymes: Modified EG2 and IndiAge® Max L contained 10138 CMCU/g and 11674 CMCU/g, respectively. Both were formulated with 13% sorbitol and 1.35% benzoate.
  Liquor ratio: 10 to 1 (3 kg denim in 30 L buffer)
  pH: 5.0+0.1 (adjusted with disodium phosphate (DSP)/Citric acid buffer)
  Temperature: 55° C.
  Treatment time: 60 minutes
  2× water rinses followed the enzyme treatment To quantify the backstaining and abrasion levels after the cellulase treatment, 8 reflectometer readings from each denim legs were taken using Chroma Meter CR-200 by Minolta. Quantitation of abrasion and backstaining performances are expressed by using the CIELAB (-b*) coordinate. CIE L* values were used to quantify the abrasion, and absolute CIE b* was used to quantify the backstaining (CIE L*: the higher the L* value, the higher the abrasion; CIE Ib*l: the higher the absolute b*, the higher the backstaining).

TABLE 2

Comparison of A and B for abrasion and backstaining on denim

| Dose u/L (CMC U/L) | Abrasion (CIE L) | | Backstaining (CIE Lb*l) | |
|---|---|---|---|---|
| | IndiAge® Max L | Modified Eg2 | IndiAge® Max L | Modified Eg2 |
| 2,500 | 27.33 | 27.56 | 9.36 | 9.39 |
| 5,000 | 28.08 | 28.32 | 10.1 | 9.56 |
| 10,000 | 29.26 | 29.69 | 9.93 | 9.93 |
| 20,000 | 30.51 | 31.27 | 10.37 | 10.17 |

These results show that the modified EGII textile processing composition has enhanced abrasion properties when compared to an endo-enriched EGII textile processing composition.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A method of treating cellulose containing fabric with cellulase comprising the steps of:
   (a) contacting said cellulose containing fabric with a treating composition comprising an effective amount of an EGII cellulase having the amino acid sequence of SEQ ID NO:1; and
   (b) incubating said cellulose containing fabric in contact with said EGII cellulase under conditions effective to treat said fabric, wherein the treatment effects an increase of abrasion of at least 0.23 CIE L value units while maintaining an equivalent level of backstaining.

2. The method according to claim 1, wherein said cellulose containing fabric comprises a cotton containing fabric.

3. The method according to claim 2, wherein said cotton containing fabric comprises dyed denim.

4. The method according to claim 1, wherein said treating composition comprises said EGII cellulase in a concentration of about 0.1 to about 1,000 ppm total protein.

5. The method according to claim 1, wherein said treating composition comprises said EGII cellulase in a concentration of about 0.2 to about 500 ppm.

6. The method according to claim 1, wherein said EGII cellulase was recombinantly expressed in a fungus or bacteria.

7. The method according to claim 6, wherein said fungus is selected from the group consisting of *Trichoderma, Penicillium, Humicola, Aspergillus*, Chrysosporium, *Fusarium*, Hypocrea, and Emericella.

8. The method according to claim 7, wherein said fungus is *Trichoderma reesei*.

9. The method according to claim 1, wherein said treating method comprises stonewashing the cellulose containing fabric and said treating composition comprises a stonewashing composition.

10. The method according to claim 9, wherein said cellulose containing fabric is colored.

11. The method according to claim 10, wherein said colored fabric is dyed denim.

12. The method according to claim 1, wherein said treating method comprises washing the cellulose containing fabric and said treating composition is a detergent composition comprising a surfactant.

13. The method according to claim 12, wherein said surfactant comprises nonionic ethoxylated alkyl phenols or nonionic ethoxylated alcohols.

* * * * *

```
SEQUENCE LISTING

<160> NUMBER OF SEQ ID NOS: 6

<210> SEQ ID NO 1
<211> LENGTH: 418
<212> TYPE: PRT
<213> ORGANISM: Artificial
<220> FEATURE:
<223> OTHER INFORMATION: synthetic modified sequence

<400> SEQUENCE: 1

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140
```

```
Asp Gly Met Thr Ile Phe Arg Leu Pro Val Gly Trp Gln Tyr Leu Val
145                 150                 155                 160
Asn Asn Asn Leu Gly Asn Leu Asp Ser Thr Ser Ile Ser Lys Tyr
            165                 170                 175
Asp Gln Leu Val Gln Gly Cys Leu Ser Leu Gly Ala Tyr Cys Ile Val
        180                 185                 190
Asp Ile His Asn Tyr Ala Arg Trp Asn Gly Gly Ile Ile Gly Gln Gly
        195                 200                 205
Gly Pro Thr Asn Ala Gln Phe Thr Ser Leu Trp Ser Gln Leu Ala Ser
    210                 215                 220
Lys Tyr Ala Ser Gln Ser Arg Val Trp Phe Gly Ile Met Asn Glu Pro
225                 230                 235                 240
His Asp Val Asn Ile Asn Thr Trp Ala Ala Thr Val Gln Glu Val Val
                245                 250                 255
Thr Ala Ile Arg Asn Ala Gly Ala Thr Ser Gln Phe Ile Ser Leu Pro
            260                 265                 270
Gly Asn Asp Trp Gln Ser Ala Gly Ala Phe Ile Ser Asp Gly Ser Ala
        275                 280                 285
Ala Ala Leu Ser Gln Val Thr Asn Pro Asp Gly Ser Thr Thr Asn Leu
        290                 295                 300
Ile Phe Asp Val His Lys Tyr Leu Asp Ser Asp Asn Ser Gly Thr His
305                 310                 315                 320
Ala Glu Cys Thr Thr Asn Asn Ile Asp Gly Ala Phe Ser Pro Leu Ala
                325                 330                 335
Thr Trp Leu Arg Gln Asn Asn Arg Gln Ala Ile Leu Thr Glu Thr Gly
            340                 345                 350
Gly Gly Asn Val Gln Ser Cys Ile Gln Asp Met Cys Gln Gln Ile Gln
        355                 360                 365
Tyr Leu Asn Gln Asn Ser Asp Val Tyr Leu Gly Tyr Val Gly Trp Gly
    370                 375                 380
Ala Gly Ser Phe Asp Ser Thr Tyr Val Leu Thr Glu Thr Pro Thr Gly
385                 390                 395                 400
Ser Gly Asn Ser Trp Thr Asp Thr Ser Leu Val Ser Ser Cys Leu Ala
                405                 410                 415
Arg Lys
```

<210> SEQ ID NO 2
<211> LENGTH: 1436
<212> TYPE: DNA
<213> ORGANISM: Artificial
<220> FEATURE:
<223> OTHER INFORMATION: synthetic modified sequence

<400> SEQUENCE: 2

```
atgaacaagt ccgtggctcc attgctgctt gcagcgtcca tactatatgg cggcgccgct      60
gcacagcaga ctgtctgggg ccagtgtgga ggtattggtt ggagcggacc tacgaattgt     120
gctcctggct cagcttgttc gaccctcaat ccttattatg cgcaatgtat tccgggagcc     180
actactatca ccacttcgac ccggccacca tccgtccaa ccaccaccac cagggctacc     240
tcaacaagct catcaactcc acccacgagc tctgggtcc gatttgccgg cgttaacatc     300
gcgggttttg actttggctg taccacagag tgagtaccc tgtttcctgg tgttgctggc     360
tgaaaagttg ggcgggtata cagcgatgcg gactgcaaga acaccgccgg tccgccacca     420
tcaagatgtg ggtggtaagc ggcggtgttt tgtacaacta cctgacagct cactcaggaa     480
ctgagaatta atggaagtct tgttacagtg gcacttgcgt tacctcgaag gtttatcctc     540
```

```
cgttgaagaa cttcaccggc tcaaacaact accccgatgg catcggccag atgcagcact    600
tcgtcaacga cgacgggatg actattttcc gcttacctgt cggatggcag tacctcgtca    660
acaacaattt gggcggcaat cttgattcca cgagcatttc aagtatgat  cagcttgttc    720 agggggtgcct gtctctgggc gcatactgca tcgtcgacat ccacaattat gctcgatgga    780
acggtgggat cattggtcag ggcggcccta ctaatgctca attcacgagc ctttggtcgc    840
agttggcatc aaagtacgca tctcagtcga gggtgtggtt cggcatcatg aatgagcccc    900
acgacgtgaa catcaacacc tgggctgcca cggtccaaga ggttgtaacc gcaatccgca    960
acgctggtgc tacgtcgcaa ttcatctctt tgcctggaaa tgattggcaa tctgctgggg   1020
ctttcatatc cgatggcagt gcagccgccc tgtctcaagt cacgaacccg gatgggtcaa   1080
caacgaatct gattttgac  gtgcacaaat acttggactc agacaactcc ggtactcacg   1140
ccgaatgtac tacaaataac attgacggcg ccttttctcc gcttgccact tggctccgac   1200
agaacaatcg ccaggctatc ctgacagaaa ccggtggtgg caacgttcag tcctgcatac   1260
aagacatgtg ccagcaaatc caatatctca accagaactc agatgtctat cttggctatg   1320
ttggttgggg tgccggatca tttgatagca cgtatgtcct gacggaaaca ccgactggca   1380
gtggtaactc atggacggac acatccttgg tcagctcgtg tctcgcaaga aagtag        1436
```

<210> SEQ ID NO 3
<211> LENGTH: 418
<212> TYPE: PRT
<213> ORGANISM: Hypocrea jecorina

<400> SEQUENCE: 3

```
Met Asn Lys Ser Val Ala Pro Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220
```

```
Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys

<210> SEQ ID NO 4
<211> LENGTH: 38
<212> TYPE: DNA
<213> ORGANISM: Artificial
<220> FEATURE:
<223> OTHER INFORMATION: synthetic primer

<400> SEQUENCE: 4
ccgcggactg cgcatcatga acaagtccgt ggctccat                        38

<210> SEQ ID NO 5
<211> LENGTH: 35
<212> TYPE: DNA
<213> ORGANISM: Artificial
<220> FEATURE:
<223> OTHER INFORMATION: synthetic primer

<400> SEQUENCE: 5
ggcgcgccct actttcttgc gagacacgag ctgac                           35

<210> SEQ ID NO 6
<211> LENGTH: 9997
<212> TYPE: DNA
<213> ORGANISM: Artificial
<220> FEATURE:
<223> OTHER INFORMATION: synthetic expression vector

<400> SEQUENCE: 6
aagcttacta gtacttctcg agctctgtac atgtccggtc gcgacgtacg cgtatcgatg    60
gcgccagctg caggcggccg cctgcagcca cttgcagtcc cgtggaattc tcacggtgaa   120
tgtaggcctt ttgtagggta ggaattgtca ctcaagcacc cccaacctcc attacgcctc   180
ccccatagag ttcccaatca gtgagtcatg gcactgttct caaatagatt ggggagaagt   240
```

```
tgacttccgc ccagagctga aggtcgcaca accgcatgat atagggtcgg caacggcaaa      300
aaagcacgtg gctcaccgaa aagcaagatg tttgcgatct aacatccagg aacctggata      360
catccatcat cacgcacgac cactttgatc tgctggtaaa ctcgtattcg ccctaaaccg      420
aagtgcgtgg taaatctaca cgtgggcccc tttcggtata ctgcgtgtgt cttctctagg      480
tgccattctt ttcccttcct ctagtgttga attgtttgtg ttggagtccg agctgtaact      540
acctctgaat ctctggagaa tggtggacta acgactaccg tgcacctgca tcatgtatat      600
aatagtgatc ctgagaaggg gggttttggag caatgtggga cttttgatggt catcaaacaa      660 agaacgaaga cgcctctttt gcaaagtttt gtttcggcta cggtgaagaa ctggatactt      720
gttgtgtctt ctgtgtattt ttgtggcaac aagaggccag agacaatcta ttcaaacacc      780
aagcttgctc ttttgagcta caagaacctg tggggtatat atctagagtt gtgaagtcgg      840
taatcccgct gtatagtaat acgagtcgca tctaaatact ccgaagctgc tgcgaacccg      900
gagaatcgag atgtgctgga aagcttctag cgagcggcta aattagcatg aaaggctatg      960
agaaattctg gagacggctt gttgaatcat ggcgttccat tcttcgacaa gcaaagcgtt     1020
ccgtcgcagt agcaggcact cattcccgaa aaaactcgga gattcctaag tagcgatgga     1080
accggaataa tataataggc aatacattga gttgcctcga cggttgcaat gcaggggtac     1140
tgagcttgga cataactgtt ccgtacccca cctcttctca acctttggcg tttccctgat     1200
tcagcgtacc cgtacaagtc gtaatcacta ttaacccaga ctgaccggac gtgttttgcc     1260
cttcatttgg agaaataatg tcattgcgat gtgtaatttg cctgcttgac cgactggggc     1320
tgttcgaagc ccgaatgtag gattgttatc cgaactctgc tcgtagaggc atgttgtgaa     1380
tctgtgtcgg gcaggacacg cctcgaaggt tcacggcaag ggaaaccacc gatagcagtg     1440
tctagtagca acctgtaaag ccgcaatgca gcatcactgg aaaatacaaa ccaatggcta     1500
aaagtacata agttaatgcc taaagaagtc atataccagc ggctaataat tgtacaatca     1560
agtggctaaa cgtaccgtaa tttgccaacg gcttgtgggg ttgcagaagc aacggcaaag     1620
ccccacttcc ccacgtttgt ttcttcactc agtccaatct cagctggtga tcccccaatt     1680
gggtcgcttg tttgttccgg tgaagtgaaa gaagacagag gtaagaatgt ctgactcgga     1740
gcgttttgca tacaaccaag ggcagtgatg gaagacagtg aaatgttgac attcaaggag     1800
tatttagcca gggatgcttg agtgtatcgt gtaaggaggt ttgtctgccg atacgacgaa     1860
tactgtatag tcacttctga tgaagtggtc catattgaaa tgtaaagtcg gcactgaaca     1920
ggcaaaagat tgagttgaaa ctgcctaaga tctcgggccc tcgggccttc ggcctttggg     1980
tgtacatgtt tgtgctccgg gcaaatgcaa agtgtggtag gatcgaacac actgctgcct     2040
ttaccaagca gctgagggta tgtgataggc aaatgttcag gggccactgc atggtttcga     2100
atagaaagag aagcttagcc aagaacaata gccgataaag atagcctcat taaacgaat      2160 gagctagtag gcaaagtcag cgaatgtgta tatataaagg ttcgaggtcc gtgcctccct     2220
catgctctcc ccatctactc atcaactcag atcctccagg agacttgtac accatctttt     2280
gaggcacaga aacccaatag tcaaccgcgg actgcgcatc atgaacaagt ccgtggctcc     2340
attgctgctt gcagcgtcca tactatatgg cggcgccgct gcacagcaga ctgtctgggg     2400
ccagtgtgga ggtattggtt ggagcggacc tacgaattgt gctcctggct cagcttgttc     2460
gaccctcaat ccttattatg cgcaatgtat tccgggagcc actactatca ccacttcgac     2520
ccggccacca tccggtccaa ccaccaccac cagggctacc tcaacaagct catcaactcc     2580
acccacgagc tctggggtcc gatttgccgg cgttaacatc gcgggttttg actttggctg     2640
```

```
taccacagag tgagtaccct tgtttcctgg tgttgctggc tgaaaagttg ggcgggtata    2700
cagcgatgcg gactgcaaga acaccgccgg tccgccacca tcaagatgtg ggtggtaagc    2760
ggcggtgttt tgtacaacta cctgacagct cactcaggaa ctgagaatta atggaagtct    2820
tgttacagtg gcacttgcgt tacctcgaag gtttatcctc cgttgaagaa cttcaccggc    2880
tcaaacaact accccgatgg catcggccag atgcagcact tcgtcaacga cgacgggatg    2940 actatttttcc gcttacctgt cggatggcag tacctcgtca acaacaattt gggcggcaat    3000
cttgattcca cgagcatttc caagtatgat cagcttgttc aggggtgcct gtctctgggc    3060
gcatactgca tcgtcgacat ccacaattat gctcgatgga acgtgggat cattggtcag    3120 ggcggcccta ctaatgctca attcacgagc ctttggtcgc agttggcatc aaagtacgca    3180
tctcagtcga gggtgtggtt cggcatcatg aatgagcccc acgacgtgaa catcaacacc    3240
tgggctgcca cggtccaaga ggttgtaacc gcaatccgca acgctggtgc tacgtcgcaa    3300
ttcatctctt tgcctggaaa tgattggcaa tctgctgggg ctttcatatc cgatggcagt    3360
gcagccgccc tgtctcaagt cacgaacccg gatgggtcaa caacgaatct gattttgac     3420 gtgcacaaat acttggactc agacaactcc ggtactcacg ccgaatgtac tacaaataac    3480
attgacggcg ccttttctcc gcttgccact tggctccgac agaacaatcg ccaggctatc    3540
ctgacagaaa ccgtggtgg caacgttcag tcctgcatac aagacatgtg ccagcaaatc    3600
caatatctca accagaactc agatgtctat cttggctatg ttggttgggg tgccggatca    3660
tttgatagca cgtatgtcct gacggaaaca ccgactggca gtggtaactc atggacggac    3720
acatccttgg tcagctcgtg tctcgcaaga aagtagggcg cgccgcgcgc cagctccgtg    3780
cgaaagcctg acgcaccggt agattcttgg tgagcccgta tcatgacggc ggcgggagct    3840
acatggcccc gggtgattta ttttttttgt atctacttct gaccctttc aaatatacgg     3900 tcaactcatc tttcactgga gatgcggcct gcttggtatt gcgatgttgt cagcttggca    3960
aattgtggct ttcgaaaaca caaaacgatt ccttagtagc catgcatttt aagataacgg    4020
aatagaagaa agaggaaatt aaaaaaaaaa aaaaacaaa catcccgttc ataacccgta     4080
gaatcgccgc tcttcgtgta tcccagtacc agtttatttt gaatagctcg cccgctggag    4140
agcatcctga atgcaagtaa caaccgtaga ggctgacacg gcaggtgttg ctagggagcg    4200
tcgtgttcta caaggccaga cgtcttcgcg gttgatatat atgtatgttt gactgcaggc    4260
tgctcagcga cgacagtcaa gttcgccctc gctgcttgtg caataatcgc agtggggaag    4320
ccacaccgtg actcccatct ttcagtaaag ctctgttggt gtttatcagc aatacacgta    4380
atttaaactc gttagcatgg ggctgatagc ttaattaccg tttaccagtg ccatggttct    4440
gcagctttcc ttggcccgta aaattcggcg aagccagcca atcaccagct aggcaccagc    4500
taaaccctat aattagtctc ttatcaacac catccgctcc cccgggatca atgaggagaa    4560 tgaggggat gcgggctaa agaagcctac ataaccctca tgccaactcc cagtttacac      4620
tcgtcgagcc aacatcctga ctataagcta acacagaatg cctcaatcct gggaagaact    4680
ggccgctgat aagcgcgccc gcctcgcaaa aaccatccct gatgaatgga aagtccagac    4740
gctgcctgcg gaagacagcg ttattgattt cccaaagaaa tcggggatcc tttcagaggc    4800
cgaactgaag atcacagagg cctccgctgc agatcttgtg tccaagctgg cggcggaga    4860 gttgacctcg gtggaagtta cgctagcatt ctgtaaacgg gcagcaatcg cccagcagtt    4920
agtagggtcc cctctacctc tcagggagat gtaacaacgc cacttatgg gactatcaag    4980 ctgacgctgg cttctgtgca gacaaactgc gcccacgagt tcttccctga cgccgctctc   5040
```

```
gcgcaggcaa gggaactcga tgaatactac gcaaagcaca agagaccgt tggtccactc    5100 catggcctcc ccatctctct caaagaccag cttcgagtca aggtacaccg ttgcccctaa    5160
gtcgttagat gtccctttt gtcagctaac atatgccacc agggctacga acatcaatg     5220 ggctacatct catggctaaa caagtacgac gaagggact cggttctgac aaccatgctc    5280
cgcaaagccg gtgccgtctt ctacgtcaag acctctgtcc cgcagaccct gatggtctgc    5340
gagacagtca acaacatcat cgggcgcacc gtcaacccac gcaacaagaa ctggtcgtgc    5400
ggcggcagtt ctggtggtga gggtgcgatc gttgggattc gtggtggcgt catcggtgta    5460
ggaacggata tcggtggctc gattcgagtg ccggccgcgt tcaacttcct gtacggtcta    5520
aggccgagtc atgggcggct gccgtatgca aagatggcga acagcatgga gggtcaggag    5580
acggtgcaca gcgttgtcgg gccgattacg cactctgttg agggtgagtc cttcgcctct    5640
tccttctttt cctgctctat accaggcctc cactgtcctc ctttcttgct ttttatacta    5700
tatacgagac cggcagtcac tgatgaagta tgttagacct ccgcctcttc accaaatccg    5760
tcctcggtca ggagccatgg aaatacgact ccaaggtcat ccccatgccc tggcgccagt    5820
ccgagtcgga cattattgcc tccaagatca agaacggcgg gctcaatatc ggctactaca    5880
acttcgacgg caatgtcctt ccacaccctc ctatcctgcg cggcgtggaa accaccgtcg    5940
ccgcactcgc caaagccggt cacaccgtga ccccgtggac gccatacaag cacgatttcg    6000
gccacgatct catctcccat atctacgcgg ctgacggcag cgccgacgta atgcgcgata    6060
tcagtgcatc cggcgagccg gcgattccaa atatcaaaga cctactgaac ccgaacatca    6120
aagctgttaa catgaacgag ctctgggaca cgcatctcca gaagtggaat taccagatgg    6180
agtaccttga gaaatggcgg gaggctgaag aaaaggccgg gaaggaactg gacgccatca    6240
tcgcgccgat tacgcctacc gctgcggtac ggcatgacca gttccggtac tatgggtatg    6300
cctctgtgat caacctgctg gatttcacga gcgtggttgt tccggttacc tttgcggata    6360
agaacatcga taagaagaat gagagtttca aggcggttag tgagcttgat gccctcgtgc    6420
aggaagagta tgatccggag gcgtaccatg gggcaccggt tgcagtgcag gttatcggac    6480
ggagactcag tgaagagagg acgttggcga ttgcagagga agtggggaag ttgctgggaa    6540
atgtggtgac tccatagcta ataagtgtca gatagcaatt tgcacaagaa atcaatacca    6600
gcaactgtaa ataagcgctg aagtgaccat gccatgctac gaaagagcag aaaaaaacct    6660
gccgtagaac cgaagagata tgacacgctt ccatctctca aaggaagaat cccttcaggg    6720
ttgcgtttcc agtctagaca cgtataacgg cacaagtgtc tctcaccaaa tgggttatat    6780
ctcaaatgtg atctaaggat ggaaagccca gaatatcgat cgcgcgcaga tccatatata    6840
gggcccgggt tataattacc tcaggtcgac gtcccatggc cattcgaatt cgtaatcatg    6900
gtcatagctg tttcctgtgt gaaattgtta tccgctcaca attccacaca acatacgagc    6960
cggaagcata aagtgtaaag cctggggtgc ctaatgagtg agctaactca cattaattgc    7020
gttgcgctca ctgcccgctt tccagtcggg aaacctgtcg tgccagctgc attaatgaat    7080
cggccaacgc gcggggagag gcggtttgcg tattgggcgc tcttccgctt cctcgctcac    7140
tgactcgctg cgctcggtcg ttcggctgcg gcgagcggta tcagctcact caaaggcggt    7200
aatacggtta tccacagaat caggggataa cgcaggaaag aacatgtgag caaaaggcca    7260
gcaaaaggcc aggaaccgta aaaaggccgc gttgctggcg ttttccata ggctccgccc     7320 ccctgacgag catcacaaaa atcgacgctc aagtcagagg tggcgaaacc cgacaggact    7380
ataaagatac caggcgtttc ccctggaag ctccctcgtg cgctctcctg ttccgaccct     7440
```

```
gccgcttacc ggatacctgt ccgcctttct cccttcggga agcgtggcgc tttctcatag   7500
ctcacgctgt aggtatctca gttcggtgta ggtcgttcgc tccaagctgg gctgtgtgca   7560 cgaaccccc  gttcagcccg accgctgcgc cttatccggt aactatcgtc ttgagtccaa   7620
cccggtaaga cacgacttat cgccactggc agcagccact ggtaacagga ttagcagagc   7680
gaggtatgta ggcggtgcta cagagttctt gaagtggtgg cctaactacg gctacactag   7740
aagaacagta tttggtatct gcgctctgct gaagccagtt accttcggaa aaagagttgg   7800
tagctcttga tccggcaaac aaaccaccgc tggtagcggt ggtttttttg tttgcaagca   7860
gcagattacg cgcagaaaaa aaggatctca agaagatcct ttgatctttt ctacggggtc   7920
tgacgctcag tggaacgaaa actcacgtta agggattttg gtcatgagat tatcaaaaag   7980
gatcttcacc tagatccttt taaattaaaa atgaagtttt aaatcaatct aaagtatata   8040
tgagtaaact tggtctgaca gttaccaatg cttaatcagt gaggcaccta tctcagcgat   8100
ctgtctattt cgttcatcca tagttgcctg actccccgtc gtgtagataa ctacgatacg   8160
ggagggctta ccatctggcc ccagtgctgc aatgataccg cgagacccac gctcaccggc   8220
tccagattta tcagcaataa accagccagc cggaagggcc gagcgcagaa gtggtcctgc   8280
aactttatcc gcctccatcc agtctattaa ttgttgccgg gaagctagag taagtagttc   8340
gccagttaat agtttcgcca acgttgttgc cattgctaca ggcatcgtgg tgtcacgctc   8400
gtcgtttggt atggcttcat tcagctccgg ttcccaacga tcaaggcgag ttacatgatc   8460
ccccatgttg tgcaaaaaag cggttagctc cttcggtcct ccgatcgttg tcagaagtaa   8520
gttggccgca gtgttatcac tcatggttat ggcagcactg cataattctc ttactgtcat   8580
gccatccgta agatgctttt ctgtgactgg tgagtactca accaagtcat tctgagaata   8640
gtgtatgcgg cgaccgagtt gctcttgccc ggcgtcaata cgggataata ccgcgccaca   8700
tagcagaact ttaaaagtgc tcatcattgg aaaacgttct cggggcgaaa actctcaag   8760 gatcttaccg ctgttgagat ccagttcgat gtaacccact cgtgcaccca actgatcttc   8820
agcatctttt actttcacca gcgtttctgg gtgagcaaaa acaggaaggc aaaatgccgc   8880
aaaaaaggga ataagggcga cacggaaatg ttgaatactc atactcttcc ttttcaata   8940 ttattgaagc atttatcagg gttattgtct catgagcgga tacatatttg aatgtattta   9000
gaaaaataaa caaatagggg ttccgcgcac atttccccga aaagtgccac ctgacgtcta   9060
agaaaccatt attatcatga cattaaccta taaaaatagg cgtatcacga ggccctttcg   9120
tctcgcgcgt ttcggtgatg acggtgaaaa cctctgacac atgcagctcc cggagacggt   9180
cacagcttgt ctgtaagcgg atgccgggag cagacaagcc cgtcagggcg cgtcagcggg   9240
tgttggcggg tgtcggggct ggcttaacta tgcggcatca gagcagattg tactgagagt   9300
gcaccataaa attgtaaacg ttaatatttt gttaaaattc gcgttaaatt tttgttaaat   9360
cagctcattt tttaaccaat aggccgaaat cggcaaaatc ccttataaat caaagaata   9420 gcccgagata gggttgagtg ttgttccagt ttggaacaag agtccactat taagaacgt   9480 ggactccaac gtcaaagggc gaaaaaccgt ctatcagggc gatggcccac tacgtgaacc   9540
atcacccaaa tcaagttttt tggggtcgag gtgccgtaaa gcactaaatc ggaaccctaa   9600
agggagcccc cgatttagag cttgacgggg aaagccggcg aacgtggcga aaaggaagg   9660 gaagaaagcg aaaggagcgg cgctagggc  gctggcaagt gtagcggtca cgctgcgcgt   9720
aaccaccaca cccgccgcgc ttaatgcgcc gctacgggc  gcgtactatg gttgctttga   9780
cgtatgcggt gtgaaatacc gcacagatgc gtaaggagaa aataccgcat caggcgccat   9840
```

```
tcgccattca ggctgcgcaa ctgttgggaa gggcgatcgg tgcgggcctc ttcgctatta    9900
cgccagctgg cgaaaggggg atgtgctgca aggcgattaa gttgggtaac gccagggttt    9960
tcccagtcac gacgttgtaa aacgacggcc agtgccc                             9997
```